US008081316B2

(12) United States Patent
de Boer et al.

(10) Patent No.: US 8,081,316 B2
(45) Date of Patent: Dec. 20, 2011

(54) PROCESS, SYSTEM AND SOFTWARE ARRANGEMENT FOR DETERMINING AT LEAST ONE LOCATION IN A SAMPLE USING AN OPTICAL COHERENCE TOMOGRAPHY

(75) Inventors: Johannes Fitzgerald de Boer, Somerville, MA (US); Boris Hyle Park, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 1639 days.

(21) Appl. No.: 11/200,228

(22) Filed: Aug. 8, 2005

(65) Prior Publication Data

US 2006/0039004 A1 Feb. 23, 2006

Related U.S. Application Data

(60) Provisional application No. 60/599,809, filed on Aug. 6, 2004.

(51) Int. Cl.
*G01B 9/02* (2006.01)
(52) U.S. Cl. ........................................... 356/497
(58) Field of Classification Search .................. 356/479, 356/497
See application file for complete search history.

(56) References Cited

U.S. PATENT DOCUMENTS

| | | | |
|---|---|---|---|
| 2,339,754 A | 1/1944 | Brace | |
| 3,090,753 A | 5/1963 | Matuszak et al. | |
| 3,601,480 A | 8/1971 | Randall | |
| 3,856,000 A | 12/1974 | Chikama | |
| 3,872,407 A | 3/1975 | Hughes | |
| 3,941,121 A | 3/1976 | Olinger | |
| 3,973,219 A | 8/1976 | Tang et al. | |
| 3,983,507 A | 9/1976 | Tang et al. | |
| 4,030,827 A | 6/1977 | Delhaye et al. | |
| 4,030,831 A | 6/1977 | Gowrinathan | |
| 4,140,364 A | 2/1979 | Yamashita et al. | |
| 4,141,362 A | 2/1979 | Wurster | |
| 4,224,929 A | 9/1980 | Furihata | |
| 4,295,738 A | 10/1981 | Meltz et al. | |
| 4,300,816 A | 11/1981 | Snitzer et al. | |

(Continued)

FOREIGN PATENT DOCUMENTS

DE 4105221 9/1991

(Continued)

OTHER PUBLICATIONS

Acioli, L. H., M. Ulman, et al. (1991). "Femtosecond Temporal Encoding in Barium-Titanate." *Optics Letters* 16(24): 1984-1986.

(Continued)

*Primary Examiner* — Hwa Lee
(74) *Attorney, Agent, or Firm* — Dorsey & Whitney LLP

(57) ABSTRACT

A system, process and software arrangement are provided to determine at least one position of at least one portion of a sample. In particular, information associated with the portion of the sample is obtained. Such portion may be associated with an interference signal that includes a first electromagnetic radiation received from the sample and a second electromagnetic radiation received from a reference. In addition, depth information and/or lateral information of the portion of the sample, may be obtained. At least one weight function can be applied to the depth information and/or the lateral information so as to generate resulting information. Further, a surface position, a lateral position and/or a depth position of the portion of the sample may be ascertained based on the resulting information.

51 Claims, 12 Drawing Sheets

U.S. PATENT DOCUMENTS

| | | |
|---|---|---|
| 4,303,300 A | 12/1981 | Pressiat et al. |
| 4,428,643 A | 1/1984 | Kay |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,650,327 A | 3/1987 | Ogi |
| 4,744,656 A | 5/1988 | Moran et al. |
| 4,751,706 A | 6/1988 | Rohde et al. |
| 4,763,977 A | 8/1988 | Kawasaki et al. |
| 4,770,492 A | 9/1988 | Levin et al. |
| 4,827,907 A | 5/1989 | Tashiro et al. |
| 4,834,111 A | 5/1989 | Khanna et al. |
| 4,868,834 A | 9/1989 | Fox et al. |
| 4,890,901 A | 1/1990 | Cross, Jr. |
| 4,892,406 A | 1/1990 | Waters |
| 4,905,169 A | 2/1990 | Buican et al. |
| 4,909,631 A | 3/1990 | Tan et al. |
| 4,925,302 A | 5/1990 | Cutler |
| 4,928,005 A | 5/1990 | Lefevre et al. |
| 4,965,441 A | 10/1990 | Picard |
| 4,965,599 A | 10/1990 | Roddy et al. |
| 4,984,888 A | 1/1991 | Tobias et al. |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,197,470 A | 3/1993 | Helfer et al. |
| 5,202,745 A | 4/1993 | Sorin et al. |
| 5,202,931 A | 4/1993 | Bacus et al. |
| 5,208,651 A | 5/1993 | Buican et al. |
| 5,212,667 A | 5/1993 | Tomlinson et al. |
| 5,214,538 A | 5/1993 | Lobb |
| 5,228,001 A | 7/1993 | Birge et al. |
| 5,241,364 A | 8/1993 | Kimura et al. |
| 5,248,876 A | 9/1993 | Kerstens et al. |
| 5,250,186 A | 10/1993 | Dollinger et al. |
| 5,262,644 A | 11/1993 | Maguire |
| 5,275,594 A | 1/1994 | Baker |
| 5,291,885 A | 3/1994 | Taniji et al. |
| 5,293,872 A | 3/1994 | Alfano et al. |
| 5,293,873 A | 3/1994 | Fang |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,404,415 A | 4/1995 | Mori et al. |
| 5,411,016 A | 5/1995 | Kume et al. |
| 5,419,323 A | 5/1995 | Kittrell et al. |
| 5,424,827 A | 6/1995 | Horwitz et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Kittrell |
| 5,526,338 A | 6/1996 | Hasman et al. |
| 5,555,087 A | 9/1996 | Miyagawa et al. |
| 5,562,100 A | 10/1996 | Kittrell et al. |
| 5,565,983 A | 10/1996 | Barnard et al. |
| 5,565,986 A | 10/1996 | Knüttel |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab et al. |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,716,324 A | 2/1998 | Toida |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,784,352 A | 7/1998 | Swanson et al. |
| 5,785,651 A | 7/1998 | Baker et al. |
| 5,795,295 A | 8/1998 | Hellmuth et al. |
| 5,801,826 A | 9/1998 | Williams |
| 5,801,831 A | 9/1998 | Sargoytchev et al. |
| 5,803,082 A | 9/1998 | Stapleton et al. |
| 5,807,261 A | 9/1998 | Benaron et al. |
| 5,810,719 A | 9/1998 | Toida |
| 5,817,144 A | 10/1998 | Gregory et al. |
| 5,836,877 A | 11/1998 | Zavislan et al. |
| 5,840,023 A | 11/1998 | Oraevsky et al. |
| 5,840,075 A | 11/1998 | Mueller et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | Dimarzio et al. |
| 6,033,721 A | 3/2000 | Nassuphis |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,091,496 A | 7/2000 | Hill |
| 6,091,984 A | 7/2000 | Perelman et al. |
| 6,107,048 A | 8/2000 | Goldenring et al. |

| | | | | | | |
|---|---|---|---|---|---|---|
| 6,111,645 | A | 8/2000 | Tearney et al. | 6,721,094 B1 | 4/2004 | Sinclair et al. |
| 6,117,128 | A | 9/2000 | Gregory | 6,738,144 B1 | 5/2004 | Dogariu et al. |
| 6,120,516 | A | 9/2000 | Selmon et al. | 6,741,355 B2 | 5/2004 | Drabarek |
| 6,134,003 | A | 10/2000 | Tearney et al. | 6,757,467 B1 | 6/2004 | Rogers |
| 6,134,010 | A | 10/2000 | Zavislan | 6,790,175 B1 | 9/2004 | Furusawa et al. |
| 6,134,033 | A | 10/2000 | Bergano et al. | 6,806,963 B1 | 10/2004 | Wälti et al. |
| 6,141,577 | A | 10/2000 | Rolland et al. | 6,816,743 B2 | 11/2004 | Moreno et al. |
| 6,151,522 | A | 11/2000 | Alfano et al. | 6,831,781 B2 | 12/2004 | Tearney et al. |
| 6,159,445 | A | 12/2000 | Klaveness et al. | 6,839,496 B1 | 1/2005 | Mills et al. |
| 6,160,826 | A | 12/2000 | Swanson et al. | 6,882,432 B2 | 4/2005 | Deck |
| 6,161,031 | A | 12/2000 | Hochman et al. | 6,903,820 B2 | 6/2005 | Wang |
| 6,166,373 | A | 12/2000 | Mao | 6,909,105 B1 | 6/2005 | Heintzmann et al. |
| 6,174,291 | B1 | 1/2001 | McMahon et al. | 6,949,072 B2 | 9/2005 | Furnish et al. |
| 6,175,669 | B1 | 1/2001 | Colston et al. | 6,961,123 B1 | 11/2005 | Wang et al. |
| 6,185,271 | B1 | 2/2001 | Kinsinger | 6,980,299 B1 | 12/2005 | de Boer |
| 6,191,862 | B1 | 2/2001 | Swanson et al. | 6,996,549 B2 | 2/2006 | Zhang et al. |
| 6,193,676 | B1 | 2/2001 | Winston et al. | 7,006,231 B2 | 2/2006 | Ostrovsky et al. |
| 6,198,956 | B1 | 3/2001 | Dunne | 7,019,838 B2 | 3/2006 | Izatt et al. |
| 6,201,989 | B1 | 3/2001 | Whitehead et al. | 7,027,633 B2 | 4/2006 | Foran et al. |
| 6,208,415 | B1 * | 3/2001 | De Boer et al. ............... 356/450 | 7,061,622 B2 | 6/2006 | Rollins et al. |
| 6,208,887 | B1 | 3/2001 | Clarke | 7,072,047 B2 | 7/2006 | Westphal et al. |
| 6,245,026 | B1 | 6/2001 | Campbell et al. | 7,075,658 B2 | 7/2006 | Izatt et al. |
| 6,249,349 | B1 | 6/2001 | Lauer | 7,099,358 B1 | 8/2006 | Chong et al. |
| 6,249,381 | B1 | 6/2001 | Suganuma | 7,113,625 B2 | 9/2006 | Watson et al. |
| 6,249,630 | B1 | 6/2001 | Stock et al. | 7,130,320 B2 | 10/2006 | Tobiason et al. |
| 6,263,234 | B1 | 7/2001 | Engelhardt et al. | 7,139,598 B2 | 11/2006 | Hull et al. |
| 6,264,610 | B1 | 7/2001 | Zhu | 7,142,835 B2 | 11/2006 | Paulus |
| 6,272,376 | B1 | 8/2001 | Marcu et al. | 7,190,464 B2 | 3/2007 | Alphonse |
| 6,274,871 | B1 | 8/2001 | Dukor et al. | 7,231,243 B2 | 6/2007 | Tearney et al. |
| 6,282,011 | B1 | 8/2001 | Tearney et al. | 7,236,637 B2 | 6/2007 | Sirohey et al. |
| 6,297,018 | B1 | 10/2001 | French et al. | 7,242,480 B2 | 7/2007 | Alphonse |
| 6,301,048 | B1 | 10/2001 | Cao et al. | 7,267,494 B2 | 9/2007 | Deng et al. |
| 6,308,092 | B1 | 10/2001 | Hoyns | 7,272,252 B2 | 9/2007 | De La Torre-Bueno et al. |
| 6,324,419 | B1 | 11/2001 | Guzelsu et al. | 7,304,798 B2 | 12/2007 | Izumi et al. |
| 6,341,036 | B1 | 1/2002 | Tearney et al. | 7,336,366 B2 | 2/2008 | Choma et al. |
| 6,353,693 | B1 | 3/2002 | Kano et al. | 7,342,659 B2 | 3/2008 | Horn et al. |
| 6,359,692 | B1 | 3/2002 | Groot | 7,355,716 B2 | 4/2008 | De Boer et al. |
| 6,374,128 | B1 | 4/2002 | Toida et al. | 7,355,721 B2 | 4/2008 | Quadling et al. |
| 6,377,349 | B1 | 4/2002 | Fercher | 7,359,062 B2 | 4/2008 | Chen et al. |
| 6,384,915 | B1 | 5/2002 | Everett et al. | 7,366,376 B2 | 4/2008 | Shishkov et al. |
| 6,393,312 | B1 | 5/2002 | Hoyns | 7,391,520 B2 | 6/2008 | Zhou et al. |
| 6,394,964 | B1 | 5/2002 | Sievert, Jr. et al. | 7,458,683 B2 | 12/2008 | Chernyak et al. |
| 6,396,941 | B1 | 5/2002 | Bacus et al. | 7,530,948 B2 | 5/2009 | Seibel et al. |
| 6,421,164 | B2 | 7/2002 | Tearney et al. | 7,609,391 B2 | 10/2009 | Betzig |
| 6,437,867 | B2 | 8/2002 | Zeylikovich et al. | 7,646,905 B2 | 1/2010 | Guittet et al. |
| 6,441,892 | B2 | 8/2002 | Xiao et al. | 7,664,300 B2 | 2/2010 | Lange et al. |
| 6,441,959 | B1 | 8/2002 | Yang et al. | 7,805,034 B2 | 9/2010 | Kato et al. |
| 6,445,485 | B1 | 9/2002 | Frigo et al. | 2001/0047137 A1 | 11/2001 | Moreno et al. |
| 6,445,944 | B1 | 9/2002 | Ostrovsky | 2002/0016533 A1 | 2/2002 | Marchitto et al. |
| 6,459,487 | B1 | 10/2002 | Chen et al. | 2002/0024015 A1 | 2/2002 | Hoffmann et al. |
| 6,463,313 | B1 | 10/2002 | Winston et al. | 2002/0048025 A1 | 4/2002 | Takaoka |
| 6,469,846 | B2 | 10/2002 | Ebizuka et al. | 2002/0048026 A1 | 4/2002 | Isshiki et al. |
| 6,475,159 | B1 | 11/2002 | Casscells et al. | 2002/0052547 A1 | 5/2002 | Toida |
| 6,475,210 | B1 | 11/2002 | Phelps et al. | 2002/0057431 A1 | 5/2002 | Fateley et al. |
| 6,477,403 | B1 | 11/2002 | Eguchi et al. | 2002/0064341 A1 | 5/2002 | Fauver et al. |
| 6,485,413 | B1 | 11/2002 | Boppart et al. | 2002/0076152 A1 | 6/2002 | Hughes et al. |
| 6,485,482 | B1 | 11/2002 | Belef | 2002/0085209 A1 | 7/2002 | Mittleman et al. |
| 6,501,551 | B1 | 12/2002 | Tearney et al. | 2002/0086347 A1 | 7/2002 | Johnson et al. |
| 6,501,878 | B2 | 12/2002 | Hughes et al. | 2002/0091322 A1 | 7/2002 | Chaiken et al. |
| 6,517,532 | B1 | 2/2003 | Altshuler et al. | 2002/0093662 A1 | 7/2002 | Chen et al. |
| 6,538,817 | B1 | 3/2003 | Farmer et al. | 2002/0109851 A1 | 8/2002 | Deck |
| 6,549,801 | B1 | 4/2003 | Chen et al. | 2002/0122246 A1 | 9/2002 | Tearney et al. |
| 6,552,796 | B2 | 4/2003 | Magnin et al. | 2002/0140942 A1 | 10/2002 | Fee et al. |
| 6,556,305 | B1 | 4/2003 | Aziz et al. | 2002/0158211 A1 | 10/2002 | Gillispie |
| 6,556,853 | B1 | 4/2003 | Cabib et al. | 2002/0161357 A1 | 10/2002 | Anderson et al. |
| 6,558,324 | B1 | 5/2003 | Von Behren et al. | 2002/0163622 A1 | 11/2002 | Magnin et al. |
| 6,564,087 | B1 | 5/2003 | Pitris et al. | 2002/0168158 A1 | 11/2002 | Furusawa et al. |
| 6,564,089 | B2 | 5/2003 | Izatt et al. | 2002/0172485 A1 | 11/2002 | Keaton et al. |
| 6,567,585 | B2 | 5/2003 | Harris | 2002/0183623 A1 | 12/2002 | Tang et al. |
| 6,593,101 | B2 | 7/2003 | Richards-Kortum et al. | 2002/0188204 A1 | 12/2002 | McNamara et al. |
| 6,611,833 | B1 | 8/2003 | Johnson et al. | 2002/0196446 A1 | 12/2002 | Roth et al. |
| 6,615,071 | B1 | 9/2003 | Casscells, III et al. | 2002/0198457 A1 | 12/2002 | Tearney et al. |
| 6,622,732 | B2 | 9/2003 | Constantz | 2003/0013973 A1 | 1/2003 | Georgakoudi et al. |
| 6,680,780 | B1 | 1/2004 | Fee | 2003/0023153 A1 | 1/2003 | Izatt et al. |
| 6,685,885 | B2 | 2/2004 | Varma et al. | 2003/0026735 A1 | 2/2003 | Nolte et al. |
| 6,687,007 | B1 | 2/2004 | Meigs | 2003/0028114 A1 | 2/2003 | Casscells, III |
| 6,687,010 | B1 | 2/2004 | Horii et al. | 2003/0030816 A1 | 2/2003 | Eom et al. |
| 6,687,036 | B2 | 2/2004 | Riza | 2003/0053673 A1 | 3/2003 | Dewaele et al. |
| 6,701,181 | B2 | 3/2004 | Tang et al. | 2003/0082105 A1 | 5/2003 | Fischman |

| | | | | | | |
|---|---|---|---|---|---|---|
| 2003/0097048 A1 | 5/2003 | Ryan et al. | EP | 1426799 | 6/2004 | |
| 2003/0108911 A1 | 6/2003 | Klimant et al. | FR | 2728343 | 8/1995 | |
| 2003/0120137 A1 | 6/2003 | Pawluczyk et al. | GB | 1257778 | 12/1971 | |
| 2003/0135101 A1 | 7/2003 | Webler | GB | 2030313 | 4/1980 | |
| 2003/0137669 A1 | 7/2003 | Rollins et al. | GB | 2209221 | 5/1989 | |
| 2003/0164952 A1 | 9/2003 | Deichmann et al. | GB | 2298054 | 8/1996 | |
| 2003/0165263 A1 | 9/2003 | Hamer et al. | JP | 6073405 | 4/1985 | |
| 2003/0171691 A1 | 9/2003 | Casscells, III et al. | JP | 20040056907 | 2/1992 | |
| 2003/0174339 A1 | 9/2003 | Feldchtein et al. | JP | 4135550 | 5/1992 | |
| 2003/0199769 A1 | 10/2003 | Podoleanu et al. | JP | 4135551 | 5/1992 | |
| 2003/0216719 A1 | 11/2003 | Debenedictis et al. | JP | 5509417 | 11/1993 | |
| 2003/0220749 A1 | 11/2003 | Chen et al. | JP | 2002214127 | 7/2002 | |
| 2003/0236443 A1 | 12/2003 | Cespedes et al. | JP | 20030035659 | 2/2003 | |
| 2004/0002650 A1 | 1/2004 | Mandrusov et al. | JP | 2007271761 | 10/2007 | |
| 2004/0054268 A1 | 3/2004 | Esenaliev et al. | WO | 7900841 | 10/1979 | |
| 2004/0072200 A1 | 4/2004 | Rigler et al. | WO | 9201966 | 2/1992 | |
| 2004/0075841 A1 | 4/2004 | Van Neste et al. | WO | 9216865 | 10/1992 | |
| 2004/0077949 A1 | 4/2004 | Blofgett et al. | WO | 9219930 | 11/1992 | |
| 2004/0086245 A1 | 5/2004 | Farroni et al. | WO | 9303672 | 3/1993 | |
| 2004/0100631 A1 | 5/2004 | Bashkansky et al. | WO | 9216865 | 10/1993 | |
| 2004/0100681 A1 | 5/2004 | Bjarklev et al. | WO | 9533971 | 12/1995 | |
| 2004/0126048 A1 | 7/2004 | Dave et al. | WO | 9628212 | 9/1996 | |
| 2004/0133191 A1 | 7/2004 | Momiuchi et al. | WO | 9732182 | 9/1997 | |
| 2004/0150829 A1 | 8/2004 | Koch et al. | WO | 9800057 | 1/1998 | |
| 2004/0150830 A1 | 8/2004 | Chan | WO | 9801074 | 1/1998 | |
| 2004/0152989 A1 | 8/2004 | Puttappa et al. | WO | 9814132 | 4/1998 | |
| 2004/0165184 A1 | 8/2004 | Mizuno | WO | 9835203 | 9/1998 | |
| 2004/0166593 A1 | 8/2004 | Nolte et al. | WO | 9838907 | 9/1998 | |
| 2004/0212808 A1 | 10/2004 | Okawa et al. | WO | 9846123 | 10/1998 | |
| 2004/0239938 A1 | 12/2004 | Izatt | WO | 9848838 | 11/1998 | |
| 2004/0246583 A1 | 12/2004 | Mueller et al. | WO | 9848846 | 11/1998 | |
| 2004/0254474 A1 | 12/2004 | Seibel et al. | WO | 9905487 | 2/1999 | |
| 2004/0263843 A1 | 12/2004 | Knopp et al. | WO | 9944089 | 2/1999 | |
| 2005/0018133 A1* | 1/2005 | Huang et al. ............ 351/205 | WO | 9944089 | 9/1999 | |
| 2005/0018201 A1 | 1/2005 | De Boer | WO | 9957507 | 11/1999 | |
| 2005/0035295 A1 | 2/2005 | Bouma et al. | WO | 0058766 | 10/2000 | |
| 2005/0046837 A1 | 3/2005 | Izumi et al. | WO | 0101111 | 1/2001 | |
| 2005/0057680 A1 | 3/2005 | Agan | WO | 0108579 | 2/2001 | |
| 2005/0057756 A1 | 3/2005 | Fang-Yen et al. | WO | 0127679 | 4/2001 | |
| 2005/0059894 A1 | 3/2005 | Zeng et al. | WO | 0138820 | 5/2001 | |
| 2005/0065421 A1 | 3/2005 | Burckhardt et al. | WO | 0142735 | 6/2001 | |
| 2005/0075547 A1 | 4/2005 | Wang | WO | 0236015 | 5/2002 | |
| 2005/0083534 A1 | 4/2005 | Riza et al. | WO | 0238040 | 5/2002 | |
| 2005/0119567 A1 | 6/2005 | Choi et al. | WO | 02053050 | 7/2002 | |
| 2005/0128488 A1 | 6/2005 | Yelin et al. | WO | 02054027 | 7/2002 | |
| 2005/0165303 A1 | 7/2005 | Kleen et al. | WO | 02084263 | 10/2002 | |
| 2005/0171438 A1 | 8/2005 | Chen et al. | WO | 03020119 | 3/2003 | |
| 2006/0103850 A1 | 5/2006 | Alphonse et al. | WO | 03046495 | 6/2003 | |
| 2006/0146339 A1 | 7/2006 | Fujita et al. | WO | 03046636 | 6/2003 | |
| 2006/0155193 A1 | 7/2006 | Leonardi et al. | WO | 03052478 | 6/2003 | |
| 2006/0164639 A1 | 7/2006 | Horn et al. | WO | 03062802 | 7/2003 | |
| 2006/0184048 A1 | 8/2006 | Saadat et al. | WO | 03105678 | 12/2003 | |
| 2006/0193352 A1 | 8/2006 | Chong et al. | WO | 2004034869 | 4/2004 | |
| 2006/0244973 A1 | 11/2006 | Yun et al. | WO | 2004057266 | 7/2004 | |
| 2007/0019208 A1 | 1/2007 | Toida et al. | WO | 2004066824 | 8/2004 | |
| 2007/0038040 A1 | 2/2007 | Cense et al. | WO | 2004088361 | 10/2004 | |
| 2007/0070496 A1 | 3/2007 | Gweon et al. | WO | 2004105598 | 12/2004 | |
| 2007/0086013 A1 | 4/2007 | De Lega et al. | WO | 2005000115 | 1/2005 | |
| 2007/0133002 A1 | 6/2007 | Wax et al. | WO | 2005047813 | 5/2005 | |
| 2007/0188855 A1 | 8/2007 | Shishkov et al. | WO | 2005054780 | 6/2005 | |
| 2007/0223006 A1 | 9/2007 | Tearney et al. | WO | 2005082225 | 9/2005 | |
| 2007/0236700 A1 | 10/2007 | Yun et al. | WO | 2006004743 | 1/2006 | |
| 2007/0291277 A1 | 12/2007 | Everett et al. | WO | 2006014392 | 2/2006 | |
| 2008/0002197 A1 | 1/2008 | Sun et al. | WO | 2006039091 | 4/2006 | |
| 2008/0007734 A1 | 1/2008 | Park et al. | WO | 2006059109 | 6/2006 | |
| 2008/0049220 A1 | 2/2008 | Izzia et al. | WO | 2006124860 | 11/2006 | |
| 2008/0097225 A1 | 4/2008 | Tearney et al. | WO | 2006130797 | 12/2006 | |
| 2009/0273777 A1 | 11/2009 | Yun et al. | WO | 2007028531 | 3/2007 | |
| | | | WO | 2007038787 | 4/2007 | |
| FOREIGN PATENT DOCUMENTS | | | WO | 2007083138 | 7/2007 | |
| DE | 4309056 | 9/1994 | WO | 2007084995 | 7/2007 | |
| DE | 19542955 | 5/1997 | | | | |
| EP | 0110201 | 6/1984 | | | | |
| EP | 0251062 | 1/1988 | | | | |
| EP | 0617286 | 2/1994 | | | | |
| EP | 0590268 | 4/1994 | | | | |
| EP | 0728440 | 8/1996 | | | | |
| EP | 0933096 | 8/1999 | | | | |
| EP | 1324051 | 7/2003 | | | | |

OTHER PUBLICATIONS

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic Range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a—Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmology Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiple Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3.

Bouma, B. E., M. Ramaswamy-Paye, et al. (1997). "Compact resonator designs for mode-locked solid-state lasers." *Applied Physics B (Lasers and Optics)* B65.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995) "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optical disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a—Optics Image Science and Vision* 5(1): 49-57.

Brosseau, C. and D. Bicout (1994). "Entropy Production in Multiple-Scattering of Light by a Spatially Random Medium." *Physical Review E* 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:A1/sub 2/0/sub 3/ laser with a multiple-pass cavity." *Optics Letters* 24(6): 417-419.

Choma, M. A., M. V. Sarunic, et al. (2003). "Sensitivity advantage of swept and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama—Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography.* Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5

Donohue, D. J., B. J. Stoyanov, et al. (1995). "Numerical Modeling of the Corneas Lamellar Structure and Birefringence Properties." *Journal of the Optical Society of America a—Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rhematology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a—Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaginge method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation.* Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry.* Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). In-vivo *dual-beam optical coherence tomography*. Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherence Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a—Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review A* 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherence tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389:503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Hellmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E—Scientific Instruments* 6(9): 822-826.

Hazebroek, H. F. and W. M. Visser (1983). "Automated Laser Interferometric Ellipsometry and Precision Reflectometry." *Journal of Physics E—Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemica-Study." *Journal of Investigative Dermatology* 104(5): 798-802.

Holland, a. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a—Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132 (1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112(12): 1584-9.

Izatt, J. A., M. D. Kulkarni, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." Journal of the *Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograghy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a—Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

Kesen, M. R., G. L. Spaeth, et al. (2002). "The Heidelberg Retina Tomograph in the diagnosis of glaucoma." American Journal of Ophthalmology 133(5): vs clinical impression 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; Knutson, Jay R. (1994). "Stationary low-coherence light imaging and spectroscopy using a CCD camera." *Proc. SPIE* , vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmology* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Opthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth-independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensations on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensationg in 1.3-1.6 Mu-M Region." *IEEE Journal of Quantum Electronics* 23(1): 59-64.

Martinez, O. E., J. P. Gordon, et al. (1984). "Negative Group-Velocity Dispersion Using Refraction." *Journal of the Optical Society of America a—Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a—Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1—Regular Papers Short Notes & Review Papers 38(5A): 2978-2982.

Molteno, a. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphirelaser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy—Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a—Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at .3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." Applied Optics 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanot, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3×3 couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a—Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence . tomography." *Journal of the Optical Society of America a—Optics Image Science and Vision* 15(9): 2288-2296.

Schmitt, J. M., S. H. Xiang, et aI. (1999). "Speckle in optical coherence tomography." *Journal of Biomedical Optics* 4(1): 95-105.

Schmitt, J. M., M. J. Yadlowsky, et al. (1995). "Subsurface Imaginge of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy.", (2000).

Smithies, D. J., T. Lindmo, et al. (1998). "Signal attenuation and localization in optical coherence tomography studies by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter-endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a—Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yabushita, H. B., B.E.; Houser, S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography.", (2000).

Yang, C., A. Wax, et al. (2001). "Phase-dispersion optical tomography." *Optics Letters* 26(10): 686-688.

Yang, C., A. Wax, et al. (2001). "Phase-referenced sensitivity applied to the study of cell interferometer with subwavelength and subhertz membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." Optics Communications 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of *Xenopus laevis.*" *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13) : 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaginge and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength-swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral-domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optical synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Liptak David C. et al., (2007) "On the Development of a Confocal Rayleigh-Brillouin Microscope" *American Institute of Physics* vol. 78, 016106.

Office Action mailed Oct. 1, 2008 for U.S. Appl. No. 11/955,986.

Invitation of Pay Additional Fees mailed Aug. 7, 2008 for International Application No. PCT/US2008/062354.

Invitation of Pay Additional Fees mailed Jul. 20, 2008 for International Application No. PCT/US2007/081982.

International Search Report and Written Opinion mailed Mar. 7, 2006 for PCT/US2005/035711.

International Search Report and Written Opinion mailed Jul. 18, 2008 for PCT/US2008/057533.

Aizu, Y et al. (1991) "Bio-Speckle Phenomena and Their Application to the Evaluation of Blood Flow" Optics and Laser Technology, vol. 23, No. 4, Aug. 1, 1991.

Richards G.J. et al. (1997) "Laser Speckle Contrast Analysis (LASCA): A Technique for Measuring Capillary Blood Flow Using the First Order Statistics of Laser Speckle Patterns" Apr. 2, 1997.

Gonick, Maria M., et al (2002) "Visualization of Blood Microcirculation Parameters in Human Tissues by Time Integrated Dynamic Speckles Analysis" vol. 972, No. 1, Oct. 1, 2002.

International Search Report and Written Opinion mailed Jul. 4, 2008 for PCT/US2008/051432.

Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "Increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19$^{th}$ Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for in vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of $CO_2$ Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interfomater Designs for Optical Coherence Tomography", IEEE Optical Fiber Sensors Conference, pp. 527-530.
Yacloob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhan et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) " A CW Tunable Near-infrared (1.085-1.175-urn) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.

Marc Nikles et al., "Brillouin gain spectrum characterization in single-mode optical fibers", Journal of Lightwave Technology 1997, 15 (10): 1842-1851.

Tsuyoshi Sonehara et al., "Forced Brillouin Spectroscopy Using Frequency-Tunable Continuous-Wave Lasers", Physical Review Letters 1995, 75 (23): 4234-4237.

Hajime Tanaka et al., "New Method of Superheterodyne Light Beating Spectroscopy for Brillouin-Scattering Using Frequency-Tunable Lasers", Physical Review Letters 1995, 74 (9): 1609-1612.

Webb RH et al. "Confocal Scanning Laser Ophthalmoscope", Applied Optics 1987, 26 (8): 1492-1499.

Andreas Zumbusch et al. "Three-dimensional vibrational imaging by coherent anti-Stokes Raman scattering", Physical Review Letters 1999, 82 (20): 4142-4145.

Katrin Kneipp et al., "Single molecule detection using surface-enhanced Raman scattering (SERS)", Physical Review Letters 1997, 78 (9): 1667-1670.

K.J. Koski et al., "Brillouin imaging" Applied Physics Letters 87, 2005.

Boas et al., "Diffusing temporal light correlation for burn diagnosis", SPIE, 1999, 2979:468-477.

David J. Briers, "Speckle fluctuations and biomedical optics: implications and applications", Optical Engineering, 1993, 32(2):277-283.

Clark et al., "Tracking Speckle Patterns with Optical Correlation", SPIE, 1992, 1772:77-87.

Facchini et al., "An endoscopic system for DSPI", Optik, 1993, 95(1):27-30.

Hrabovsky, M., "Theory of speckle dispacement and decor: elation: application in mechanics", SPIE, 1998, 3479:345-354.

Sean J. Kirkpatrick et al., "Micromechanical behavior of cortical bone as inferred from laser speckle data", Journal of Biomedical Materials Research, 1998, 39(3):373-379.

Sean J. Kirkpatrick et al., "Laser speckle microstrain measurements in vascular tissue", SPIE, 1999, 3598:121-129.

Loree et al., "Mechanical Properties of Model Atherosclerotic Lesion Lipid Pools", Arteriosclerosis and Thrombosis, 1994, 14(2):230-234.

Podbielska, H. "Interferometric Methods and Biomedical Research", SPIE, 1999, 2732:134-141.

Richards-Kortum et al., "Spectral diagnosis of atherosclerosis using an optical fiber laser catheter", American Heart Journal, 1989, 118(2):381-391.

Ruth, B. "Blood flow determination by the laser speckle method", Int J Microcirc: Clin Exp, 1990, 9:21-45.

Shapo et al., "Intravascular strain imaging: Experiments on an Inhomogeneous Phantom", IEEE Ultrasonics Symposium 1996, 2:1177-1180.

Shapo et al., "Ultrasonic displacement and strain imaging of coronary arteries with a catheter array", IEEE Ultrasonics Symposium 1995, 2:1511-1514.

Thompson et al., "Imaging in scattering media by use of laser speckle", Opt. Soc. Am. A., 1997, 14(9):2269-2277.

Thompson et al., "Diffusive media characterization with laser speckle", Applied Optics, 1997, 36(16):3726-3734.

Tuchin, Valery V., "Coherent Optical Techniques for the Analysis of Tissue Structure and Dynamics," Journal of Biomedical Optics, 1999, 4(1):106-124.

M. Wussling et al., "Laser diffraction and speckling studies in skeletal and heart muscle", Biomed, Biochim, Acta, 1986, 45(1/2):S 23-S 27.

T. Yoshimura et al., "Statistical properties of dynamic speckles", J. Opt. Soc. Am A. 1986, 3(7):1032-1054.

Zimnyakov et al., "Spatial speckle correlometry in applications to tissue structure monitoring", Applied Optics 19976, 36(22): 5594-5607.

Zimnyakov et al., "A study of statistical properties of partially developed speckle fields as applied to the diagnosis of structural changes in human skin", Optics and Spectroscopy, 1994, 76(5): 747-753.

Zimnyakov et al., "Speckle patterns polarization analysis as an approach to turbid tissue structure monitoring", SPIE 1999, 2981:172-180.

Ramasamy Manoharan et al., "Biochemical analysis and mapping of atherosclerotic human artery using FT-IR microspectroscopy", Atherosclerosis, May 1993, 181-1930.

N.V. Salunke et al., "Biomechanics of Atherosclerotic Plaque" Critical Reviews™ in Biomedical Engineering 1997, 25(3):243-285.

D. Fu et al., "Non-invasive quantitative reconstruction of tissue elasticity using an iterative forward approach", Phys. Med. Biol. 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740.

International Written Opinion for International Patent application No. PCT/US2005/039740.

International Search Report for International Patent application No. PCT/US2005/030294.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics 19, 1998, pp. 107-117.

Lauer, V. "New approach to optical diffraction tomography yielding a vector equation of diffraction tomography and a novel tomographic microscope", Journal of Microscopy vol. 205, Issue 2. 2002. pp. 165-176.

Yu, P. et al. "Imaging of tumor necroses using full-frame optical coherence imaging", Proceedings of SPIE vol. 4956, 2003, pp. 34-41.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Office Action dated Dec. 18, 2006 for U.S. Appl. No. 10/501,276.

Devesa, Susan S. et al. (1998) "Changing Patterns in the Incidence of Esophegeal and Gastrin Carcinoma in the United States." American Cancer Society vol. 83, No. 19 pp. 2049-2053.

Barr, H et al. (2005) "Endoscopic Therapy for Barrett's Oesophaugs" Gut vol. 54:875-884.

Johnston, Mark H.(2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" Gastrorenterology vol. 112, pp. 1787-1797.

Sepchler, Stuart Jon. (1997) "Barrett's Esophagus: Should We Brush off this Balloning Problem?" Gastroenterology vol. 112, pp. 2138-2152.

Froehly, J. et al. (2003) "Multiplexed 3D Imaging Using Wavelength Encoded Spectral Interferometry: A Proof of Principle" Optics Communications vol. 222, pp. 127-136.

Kubba A.K. et al. (1999) "Role of p53 Assessment in Management of Barrett's Esophagus" Digestive Disease and Sciences vol. 44, No. 4. pp. 659-667.

Reid, Brian J. (2001) "p53 and Neoplastic Progression in Barrett's Esophagus" The American Journal of Gastroenterology vol. 96, No. 5, pp. 1321-1323.

Sharma, P. et al.(2003) "Magnification Chromoendoscopy for the Detection of Intestinal Metaplasia and Dysplasia in Barrett's Oesophagus" Gut vol. 52, pp. 24-27.

Kuipers E.J et al. (2005) "Diagnostic and Therapeutic Endoscopy" Journal of Surgical Oncology vol. 92, pp. 203-209.

Georgakoudi, Irene et al. (2001) "Fluorescence, Reflectance, and Light-Scattering Spectroscopy for Evaluating Dysplasia in Patients with Barrett's Esophagus" Gastroenterology vol. 120, pp. 1620-1629.

Adrain, Alyn L. et al. (1997) "High-Resolution Endoluminal Sonography is a Sensitive Modality for the Identification of Barrett's Meaplasia" Gastrointestinal Endoscopy vol. 46, No. 2, pp. 147-151.

Canto, Marcia Irene et al (1999) "Vital Staining and Barrett's Esophagus" Gastrointestinal Endoscopy vol. 49, No. 3, part 2, pp. 12-16.

Evans, John A. et al. (2006) "Optical Coherence Tomogrpahy to Identify Intramucosal Carcinoma and High-Grade Dysplasia in Barrett's Esophagus" *Clinical Gastroenterology and Hepatology* vol. 4, pp. 38-3.

Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Balloon-based Bipolar Electrode: A Phase Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103 pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis Precise Microsurgery by Selective Absorption of Pulsed Radiation" *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acosustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No. 7, pp. 1200-1209.

Jerath, Maya R. et al (1992) "Dynamic Optical Property ChangeS: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis Ablation of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

International Written Opinion for International Patent application No. PCT/US2005/043951.

International Search Report for International Patent application No. PCT/US2005/043951.

Erdelyi et al. "Generation of diffraction-free beams for applications in optical microlithography", J. Vac. Sci. Technol. B 15 (12), Mar./Apr. 1997, pp. 287-292.

International Search Report for International Patent application No. PCT/US2005/023664.

International Written Opinion for International Patent application No. PCT/US2005/023664.

Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.

International Search Report for International Patent application No. PCT/US2001/049704.

International Search Report for International Patent application No. PCT/US2004/039454.

International Written Opinion for International Patent application No. PCT/US2004/039454.

PCT International Preliminary Report on Patentability for International Application No. PCT/US2004/038404 dated Jun. 2, 2006.

Jujimoto et al., "High Resolution in Vivo Intra-Arterial Imaging with Optical Coherence Tomography", *Official Journal of the British Cardiac Society*, vol. 82, pp. 128-133 Heart, 1999.

D. Huang et al., "Optical Coherence Tomography", *Science*, vol. 254, pp. 1178-1181, Nov. 1991.

Tearney et al., "High-Speed Phase—and Delay Scanning with a Grating Based Phase Control Delay Line", *Optics Letters*, vol. 22, pp. 1811-1813, Dec. 1997.

Rollins, et al., "In Vivo Video Rate Optical Coherence Tomography", *Optics Express*, vol. 3, pp. 219-229, Sep. 1998.

Saxer, et al., High Speed Fiber-Based Polarization-Sensitive Optical Coherence Tomography of in Vivo Human Skin, *Optical Society of America*, vol. 25, pp. 1355-1357, Sep. 2000.

Oscar Eduardo Martinez, "3000 Times Grating Compress or with Positive Group Velocity Dispersion", *IEEE*, vol QE-23, pp. 59-64, Jan. 1987.

Kulkarni, et al., "Image Enhancement in Optical Coherence Tomography Using Deconvolution", *Electronics Letters*, vol. 33, pp. 1365-1367, Jul. 1997.

Bashkansky, et al., "Signal Processing for Improving Field Cross-Correlation Function in Optical Coherence Tomography", *Optics & Photonics News*, vol. 9, pp. 8137-8138, May 1998.

Yung et al., "Phase-Domain Processing of Optical Coherence Tomography Images", *Journal of Biomedical Optics*, vol. 4, pp. 125-136, Jan. 1999.

Tearney, et al., "In Vivo Endoscopic Optical Biopsy with Optical Coherence Tomography", *Science*, vol. 276, Jun. 1997.

W. Drexler et al., "In Vivo Ultrahigh-Resolution Optical Coherence Tomography", Opt. Lett. vol. 24, pp. 1221-1223, Sep. 1999.

Nicusor V. Iftimia et al., "A Portable, Low Coherence Interferometry Based Instrument for Fine Needle Aspiration Biopsy Guidance" Accepted to Review of Scientific Instruments, 2005.

Abbas, G.L., V.W.S. Chan et al., "Local-Oscillator Excess-Noise Suppression for Homodyne and Heterodyne-Detection", *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers", *Journal of the Optical Society of America B—Optical Physics*, vol. 5, pp. 147-159, Jan. 1998.

Andretzky, P. et al., "Optical Coherence Tomography by Spectral Radar: Improvement of Signal-to-Noise Ratio", *The International Society for Optical Engineering*, USA, vol. 3915, 2000.

Ballif, J. et al., "Rapid and Scalable Scans at 21 m/s in optical Low-Coherence Reflectometry", *Optics Letters*, vol. 22, pp. 757-759, Jun. 1997.

Barfuss H. et al., "Modified Optical Frequency-Domain Resolution with High-Spatial-Resolution for Components of Integrated Optic Systems", *Journal of Lightwave Technology*, vol. 7, pp. 3-10, Jan. 1989.

Beaud, P. et al., "Optical Reflectometry with Micrometer Resolution for the Investigation of Integrated Optical-Devices", *Ieee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography", *Optics Letters*, vol. 24, pp. 531-533, Apr. 1999.

Brinkmeyer, E. et al., "Efficient Algorithm for Non-Equidistant Interpolation of Sampled Data", *Electronics Letters*, vol. 28, p. 693, Mar. 1992.

Brinkmeyer, E. et al., "High-Resolution OCDR in Dispersive Wave-Guides", *Electronics Letters*, vol. 26, pp. 413-414, Mar. 1990.

Chinn, S.R. et al., "Optical Coherence Tomography Using a Frequency-Tunable Optical Source", *Optics Letters*, vol. 22, pp. 340-342, Mar. 1997.

Danielson, B.L. et al., "Absolute Optical Ranging Using Low Coherence Interferometry", *Applied Optics*, vol. 30, p. 2975, Jul. 1991.

Dorrer, C. et al., "Spectral Resolution and Sampling Issues in Fourier-Transform Spectral Interferometry", *Journal of the Optical Society of America B—Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments", *Optics Express*, vol. 10, p. 1215, Oct. 2002.

Eickhoff, W. et al., "Optical Frequency-Domain Reflectometry in Single-Mode Fiber", *Applied Physics Letters*, vol. 39, pp. 693-695, 1981.

Fercher, Adolf "Optical Coherence Tomography", *Journal of Biomedical Optics*, vol. 1, pp. 157-173, Apr. 1996.

Ferreira, L.A. et al., "Polarization-Insensitive Fiberoptic White-Light Interferometry", *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver", *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides", *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser", *Optics Letters*, vol. 11, pp. 1704-1706, Nov. 1997.

Haberland, U. H. P. et al., "Chirp Optical Coherence Tomography of Layered Scattering Media", *Journal of Biomedical Optics*, vol. 3, pp. 259-266, Jul. 1998.

Hammer, Daniel X. et al., "Spectrally Resolved White-Light Interferometry for Measurement of Ocular Dispersion", *Journal of the Optical Society of America A—Optics Image Science and Vision*, vol. 16, pp. 2092-2102, Sep. 1999.

Harvey, K. C. et al., "External-Cavity Diode-Laser Using a Grazing-Incidence Diffraction Grating", *Optics Letters*, vol. 16, pp. 910-912, Jun. 1991.

Hausler, Gerd et al., "'Coherence Radar' and 'Spectral Radar' New Tools for Dermatological Diagnosis", *Journal of Biomedical Optics*, vol., 3, pp. 21-31, Jan. 1998.

Hee, Michael R. et al., "Polarization-Sensitive Low-Coherence Reflectometer for Birefringence Characterization and Ranging", *Journal of the Optical Society of America B (Optical Physics)*, vol. 9, p. 903-908, Jun. 1992.

Hotate Kazuo et al., "Optical Coherence Domain Reflectometry by Synthesis of Coherence Function", *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier", *Applied Physics Letters*, vol. 51, pp. 1051-1053, 1987.

Ivanov, A. P. et al., "New Method for High-Range Resolution Measurements of Light Scattering in Optically Dense Inhomogeneous Media", *Optics Letters*, vol. 1, pp. 226-228, Dec. 1977.

Ivanov, A. P. et al., "Interferometric Study of the Spatial Structure of a Light-Scattering Medium", *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths", *Applied Optics*, vol. 22, pp. 706-710, Mar. 1983.

Kersey, A. D. et al., "Adaptive Polarization Diversity Receiver Configuration for Coherent Optical Fiber Communications", *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm", *Journal of Lightwave Technology*, vol. 9, pp. 1493-1502, Nov. 1991.

Larkin, Kieran G., "Efficient Nonlinear Algorithm for Envelope Detection in White Light Interferometry", *Journal of the Optical Society of America A—Optics Image Science and Vision*, vol. 13, pp. 832-843, Apr. 1996.

Leitgeb, R. et al., "Spectral measurement of Absorption by Spectroscopic Frequency-Domain Optical Coherence Tomography", *Optics Letters*, vol. 25, pp. 820-822, Jun. 2000.

Lexer, F. et al., "Wavelength-Tuning Interferometry of Intraocular Distances", *Applied Optics*, vol. 36, pp. 6548-6553, Sep. 1997.

Mitsui, Takahisa, "Dynamic Range of Optical Reflectometry with Spectral Interferometry", *Japanese Journal of Applied Physics Part 1—Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlated Generated by White Light", *Optics Letters*, vol. 15, pp. 393-395, Apr. 1990.

Okoshi, Takanori, "Polarization-State Control Schemes for Heterodyne or Homodyne Optical Fiber Communications", *Journal of Lightwave Technology*, vol. LT-3, pp. 1232-1237, Dec. 1995.

Passy, R. et al., "Experimental and Theoretical Investigations of Coherent OFDR with Semiconductor-Laser Sources", *Journal of Lightwave Technology*, vol. 12, pp. 1622-1630, Sep. 1994.

Podoleanu, Adrian G., "Unbalanced Versus Balanced Operation in an Optical Coherence Tomography System", *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier", *Journal of the Optical Society of America B—Optical Physics*, vol. 19, pp. 1286-1294, Jun. 2002.

Schmitt, J. M. et al, "Measurement of Optical-Properties O Biological Tissues by Low-Coherence Reflectometry" *Applied Optics*, vol. 32, pp. 6032-6042, Oct. 1993.
Silberberg, Y. et al., "Passive-Mode Locking of a Semiconductor Diode-Laser", *Optics Letters*, vol. 9, pp. 507-509, Nov. 1984.
Smith, L. Montgomery et al., "Absolute Displacement Measurements Using Modulation of the Spectrum of White-Light in a Michelson Interferometer", *Applied Optics*, vol. 28, pp. 3339-3342, Aug. 1989.
Sonnensc, C. M. et al., "Signal-to-Noise Relationships for Coaxial Systems that Heterodyne Backscatter from Atmosphere", *Applied Optics*, vol. 10, pp. 1600-1604, Jul. 1971.
Sorin, W. V. et al., "Measurement of Rayleigh Backscattering at 1.55 mu m with 32 mu m Spatial Resolution", *IEEE Photonics Technology Letters*, vol. 4, pp. 374-376, Apr. 1992.
Sorin, W. V. et al., "A Simple Intensity Noise-Reduction Technique for Optical Low-Coherence Reflectometry", *IEEE Photonics Technology Letters*, vol. 4, pp. 1404-1406, Dec. 1992.
Swanson, E. A. et al., "High-Speed Optical Coherence Domair Reflectometry", *Optics Letters*, vol. 17, pp. 151-153, Jan. 1992.
Takada, K. et al., "High-Resolution OFDR with Incorporated Fiberoptic Frequency Encoder", *IEEE Photonics Technology Letters*, vol. 4, pp. 1069-1072, Sep. 1992.
"Narrow-Band light Source with Acoustooptic Tunable Filter for Optical Low-Coherence Reflectometry", by Takada, Kazumasa et al., *IEEE Photonics Technology Letters*, vol. 8, pp. 658-660, May 1996.
Takada, Kazumasa et al., "New Measurement System for Fault Location in Optical Wave-Guide Devices Based on an Intermetric-Technique", *Applied Optics*, vol. 26, pp. 1603-1606, May 1987.
Tateda, Mitsuhiro et al., "Interferometric Method for Chromatic Dispersion Measurement in a Single-Mode Optical Fiber", *IEEE Journal of Quantum Electronics*, vol. 17, pp. 404-407, Mar. 1981.
Toide, M. et al., "Two-Dimensional Coherent Detection Imaging in Multiple Scattering Media Based the Directional Resolution Capability of the Optical Heterodyne Method", *Applied Physics B (Photophysics and Laser Chemistry)*, vol. B52, pp. 391-394, 1991.
Trutna, W. R. et al., "Continuously Tuned External-Cavity Semiconductor-Laser", *Journal of Lightwave Technology*, vol. 11, pp. 1279-1286, Aug. 1993.
Uttam, Deepak et al., "Precision Time Domain Reflectometry in Optical Fiber Systems Using a Frequency Modulated Continuous Wave Ranging Technique", Journal of *Lightwave Technology*, vol. 3, pp. 971-977, Oct. 1985.
Von Der Weid, J. P. et al., "On the Characterization with Optical Fiber Network Components with Optical Frequency Domain Reflectometry", Journal of *Lightwave Technology*, vol. 15, pp. 1131-1141, Jul. 1997.
Wysocki, P.F. et al., "Broad-Spectrum, Wavelength-Swept, Erbium-Doped Fiber Laser at 1.55-Mu-M", *Optics Letters*, vol. 15, pp. 879-881, Aug. 1990.
Youngquist, Robert C. et al., "Optical Coherence-Domain Reflectometry—A New Optical Evaluation Technique", *Optics Letters*, vol. 12, pp. 158-160, Mar. 1987.
Yun, S. H. et al., "Wavelength-Swept Fiber Laser with Frequency Shifted Feedback and Resonantly Swept Intra-Cavity Acoustooptic Tunable Filter", *IEEE Journal of Selected Topics in Quantum Electronics*, vol. 3, pp. 1087-1096, Aug. 1997.
Yun, S. H. et al., "Interrogation of Fiber Grating Sensor Arrays with a Wavelength-Swept Fiber Laser", *Optics Letters*, vol. 23, pp. 843-845, Jun. 1998.
Yung, K. M., "Phase-Domain Processing of Optical Coherence Tomography Images", *Journal of Biomedical Optics*, vol. 4, pp. 125-136, Jan. 1999.
Zhou, Xiao-Qun et al., "Extended-Range FMCW Reflectometry Using an optical Loop with a Frequency Shifter", *IEEE Photonics Technology Letters*, vol. 8, pp. 248-250, Feb. 1996.
Zorabedian, Paul et al., "Tuning Fidelity of Acoustooptically Controlled External Cavity Semiconductor-Lasers", *Journal of Lightwave Technology*, vol. 13, pp. 62-66, Jan. 1995.
Victor S. Y. Lin et al., "A Porous Silicon-Based Optical Interferometric Biosensor", *Science Magazine*, vol. 278, pp. 840-843, Oct. 31, 1997.

Notice of Reasons for Rejection and English translation for Japanese Patent Application No. 2002-538830.
De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.
Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.
Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.
Roth, Jonathan E. et al., "Simplified Method for Polarization-Sensitive Optical Coherence Tomography," *Optics Letters*, vol. 26, No. 14, Jul. 15, 2001, pp. 1069-1071.
Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.
Wong, Brian J.F. et al., "Optical Coherence Tomography of the Rat Cochlea," Journal of *Biomedical Optics*, vol. 5, No. 4, Oct. 2000, pp. 367-370.
Yao, Gang et al., "Propagation of Polarized Light in Turbid Media: Simulated Animation Sequences," *Optics Express*, vol. 7, No. 5, Aug. 28, 2000, pp. 198-203.
Wang, Xiao-Jun et al., "Characterization Dentin and Enamel by Use of Optical Coherence Tomography," *Applied Optics*, vol. 38, No. 10, Apr. 1, 1999, pp. 2092-2096.
De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.
Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.
Groner, Warren et al., "Orthogonal Polarization Spectral Imaging: A New Method for Study of the Microcirculation," *Nature Medicine Inc.*, vol. 5 No. 10, Oct. 1999, pp. 1209-1213.
De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.
Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.
Lu, Shih-Yau et al., "Homogeneous and Inhomogeneous Jones Matrices," *J. Opt. Soc. Am. A.*, vol. 11, No. 2, Feb. 1994, pp. 766-773.
Bickel, S. William et al., "Stokes Vectors, Mueller Matrices, and Polarized Scattered Light," *Am. J. Phys.*, vol. 53, No. 5, May 1985 pp. 468-478.
Brehonnet, F. Le Roy et al., "Optical Media and Target Characterization by Mueller Matrix Decomposition," *J. Phys. D: Appl. Phys.* 29, 1996, pp. 34-38.
Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.
De Boer, Johannes F. et al., "Two-Dimensional Birefringence Imaging in BIological Tissue by Polarization-Sensitive Optical Coherence Tomography," *Optics Letters*, vol. 22, No. 12, Jun. 15, 1997, pp. 934-936.
De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.
Everett, M.J. et al., "Birefringence Characterization of Biological Tissue by Use of Optical Coherence Tomography," *Optics Letters*, vol. 23, No. 3, Feb. 1, 1998, pp. 228-230.
Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.
Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," Optics Letters, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," Applied Optics, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," Optics Letters, vol. 27, No. 17, Sep. 1, 2002, pp. 1534-1536.

De Boer, Johannes F. et al., "Review of Polarization Sensitive Optical Coherence Tomography and Stokes Vector Determination," Journal of Biomedical Optics, Jul. 2002, vol. 7, No. 3, pp. 359-371.

Fried, Daniel et al., "Imaging Caries Lesions and Lesion Progression with Polarization Sensitive Optical Coherence Tomography," Journal of Biomedical Optics, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," Optics Letters, vol. 27, No. 2, Jan. 15, 2002, pp. 101-103.

Jiao, Shuliang et al., "Jones-Matrix Imaging of Biological Tissues with Quadruple-Channel Optical Coherence Tomography," Journal of Biomedical Optics, vol. 7, No. 3, Jul. 2002, pp. 350-358.

Kuranov, R.V. et al., "Complementary Use of Cross-Polarization and Standard OCT for Differential Diagnosis of Pathological Tissues," Optics Express, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," Optics Letters, vol. 27, No. 18, Sep. 15, 2002, pp. 1610-1612.

ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," Optics Letters, vol. 27, No. 19, Oct. 1, 2002, pp. 1702-1704.

Tripathi, Renu et al., "Spectral Shaping for Non-Gaussian Source Spectra in Optical Coherence Tomography," Optics Letters, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," Optics Letters, vol. 27, No. 20, Oct. 15, 2002, pp. 1803-1805.

White, Brian R. et al., "In Vivo Dynamic Human Retinal Blood Flow Imaging Using Ultra-High-Speed Spectral Domain Optical Doppler Tomography," Optics Express, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," Optics Letters, vol. 28, No. 21, Nov. 1, 2003, pp. 2067-2069.

Jiao, Shuliang et al., "Optical-Fiber-Based Mueller Optical Coherence Tomography," Optics Letters, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," Applied Optics, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," Applied Optics, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," Applied Optics, vol. 42, No. 19, Jul. 1, 2003, pp. 3811-3818.

Morgan, Stephen P. et al., "Surface-Reflection Elimination in Polarization Imaging of Superficial Tissue," Optics Letters, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," Optics Express, vol. 11, No. 14, Jul. 14, 2003, pp. 1669-1676.

Park, B. Hyle et al., "Real-Time Multi-Functional Optical Coherence Tomography," Optics Express, vol. 11, No. 7, Apr. 7, 2003, pp. 782-793.

Shribak, Michael et al., "Techniques for Fast and Sensitive Measurements of Two-Dimensional Birefringence Distributions," Applied Optics, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," Elsevier, Optics Communications, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Ranging of Birefringence," Optics Letters, vol. 28, No. 19, Oct. 1, 2003, pp. 1775-1777.

Yang, Ying et al., "Observations of Birefringence in Tissues from Optic-Fibre-Based Optical Coherence Tomography," Measurement Science and Technology, Nov. 2002, pp. 41-46.

Yun, S.H. et al., "High-Speed Optical Frequency-Domain Imaging," Optics Express, vol. 11, No. 22, Nov. 3, 2003, pp. 2953-2963.

Yun, S.H. et al., "High-Speed Spectral-Domain Optical Coherence Tomography at 1.3 µm Wavelength," Optics Express, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," Optics Express, vol. 11, No. 24, Dec. 1, 2003, pp. 3262-3270.

Pircher, Michael et al., "Three Dimensional Polarization Sensitive OCT of Human Skin in Vivo," 2004, Optical Society of America.

Götzinger, Erich et al., "Measurement and Imaging of Birefringent Properties of the Human Cornea with Phase-Resolved, Polarization-Sensitive Optical Coherence Tomography," Journal of Biomedical Optics, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," Optics Letters, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," Investigative Ophthalmology & Visual Science, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," Physics in Medicine and Biology, 2004, pp. 1295-1306.

Nassif, Nader et al., "In Vivo Human Retinal Imaging by Ultrahigh-Speed Spectral Domain Optical Coherence Tomography," Optics Letters, vol. 29, No. 5, Mar. 1, 2004, pp. 480-482.

Nassif, N.A. et al., "In Vivo High-Resolution Video-Rate Spectral-Domain Optical Coherence Tomography of the Human Retina and Optic Nerve," Optics Express, vol. 12, No. 3, Feb. 9, 2004, pp. 367-376.

Park, B. Hyle et al., "Comment on Optical-Fiber-Based Mueller Optical Coherence Tomography," Optics Letters, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optical Components," Optics Letters, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," Elsevier, Burns, 2004, pp. 511-517.

Pierce, Mark C. et al., "Advances in Optical Coherence Tomography Imaging for Dermatology," The Society for Investigative Dermatology, Inc. 2004, pp. 458-463.

Pierce, Mark C. et al., "Birefringence Measurements in Human Skin Using Polarization-Sensitive Optical Coherence Tomography," Journal of Biomedical Optics, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," Journal of Biomedical Optics, vol. 9, No. 1, Jan./Feb. 2004, pp. 121-125.

Pircher, Michael et al., "Imaging of Polarization Properties of Human Retina in Vivo with Phase Resolved Transversal PS-OCT," Optics Express, vol. 12, No. 24, Nov. 29, 2004 pp. 5940-5951.
Pircher, Michael et al., "Transversal Phase Resolved Polarization Sensitive Optical Coherence Tomography," Physics in Medicine & Biology, 2004, pp. 1257-1263.
Srinivas, Shyam M. et al., "Determination of Burn Depth by Polarization-Sensitive Optical Coherence Tomography," Journal of Biomedical Optics, vol. 9, No. 1, Jan./Feb. 2004, pp. 207-212.
Strasswimmer, John et al., "Polarization-Sensitive Optical Coherence Tomography of Invasive Basal Cell Carcinoma," Journal of Biomedical Optics, vol. 9, No. 2, Mar./Apr. 2004, pp. 292-298.
Todorovie, Milog et al., "Determination of Local Polarization Properties of Biological Samples in the Presence of Diattentuation by use of Mueller Optical Coherence Tomography," Optics Letters, vol. 29, No. 20, Oct. 15, 2004, pp. 2402-2404.
Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.
ffice Action dated Aug. 24, 2006 for U.S. Appl. No. 10/137,749.
Barry Cense et al., "Spectral-domain polarization-sensitive optical coherence tomography at 850nm", Coherence Domain Optical Methods and Optical Coherence Tomography in Biomedicine IX, 2004, pp. 159-162.
A. Ymeti et al., "Integration of microfluidics with a four-channel integrated optical Young interferometer immunosensor", Biosensors and Bioelectronics, Elsevier Science Publishers, 2005, pp. 1417-1421.
PCT International Search Report for Application No. PCT/US2006/018865 filed May 5, 2006.
International Written Opinion for International Patent application No. PCT/US2006/018865 filed May 5, 2006.
John M. Poneros, "Diagnosis of Barrett's esophagus using optical coherence tomography", Gastrointestinal Endoscopy clinics of North America, 14 (2004) pp. 573-588.
P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.
Ko T et al., "Ultrahigh resolution in vivo versus ex vivo OCT imaging and tissue preservation", Conference on Lasers and electro-optics, 2001, pp. 252-253.
Paul M. Ripley et al., "A comparison of Artificial Intelligence techniques for spectral classification in the diagnosis of human pathologies based upon optical biopsy", Journal of Optical Society of America, 2000, pp. 217-219.
Wolfgang Drexler et al., "Ultrahigh-resolution optical coherence tomography", Journal of Biomedical Optics SPIE USA, 2004, pp. 47-74.
PCT International Search Report for Application No. PCT/US2006/016677 filed Apr. 28, 2006.
International Written Opinion for International Patent application No. PCT/US2006/016677 filed Apr. 28, 2006.
Office Action dated Nov. 13, 2006 for U.S. Appl. No. 10/501,268.
Office Action dated Nov. 20, 2006 for U.S. Appl. No. 09/709,162.
PCT International Search Report and Written Opinion for Application No. PCT/US2004/023585 filed Jul. 23, 2004.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.

D.J. Bowery et al., (1999) "Patterns of Gastritis in Patients with Gastro-Oesophageal Reflux Disease,", Gut, vol. 45, pp. 798-803.
O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia-Dysphasia-Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., "Applications of Fourier Transform Infrared Imaging Microscopy in Neurotoxicity", Annals New York Academy of Sciences, pp. 234-246, 1997.
Joo, Chulmin et al., Spectral-domain optical coherence phase microscopy for quantitative phase-contrast imaging, Optics Letters, Aug. 15, 2005, vol. 30, No. 16, pp. 2131-2133.

Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., "Speckle in Optical Coherence Tomography: An Overview", SPIE vol. 3726, pp. 450-461, 1999.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the Spie—The International Society for Optical Engineering SPIE—vol. 4001, 2000, pp. 92-101.
Lisauskas B. Jennifer et al., "Investigation of Plaque Biomechanics from Intravascular Ultrasound Images using Finite Element Modeling", Proceedings of the $19^{th}$ International Conference — IEEE Oct. 30-Nov. 2 1997, pp. 887-888.
Parker K. J. et al., "Techniques for Elastic Imaging: A Review", IEEE Engineering in Medicine and Biology, Nov./Dec. 1996, pp. 52-59.
European Patent Office Search Report for Application No. 05791226.3, (2001).
Dubois Arnaud et al., "Ultrahigh-resolution OCT using white-light interference microscopy", Proceedings of SPIE, 2003, vol. 4956, pp. 14-21.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic. plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
Wojtkowski et al., "In Vivo Human Retinal Imaging by Fourier Domain Optical Coherence Tomography", Journal of Biomedical Optics 7(3), pp. 457-463, (2002).
B. Hermann et al., "Precision of extracting absorption profiles from weakly scattering media with spectroscopic time-domain optical coherence tomography," Opt. Express 12(8), 1677-88, (2004).
B.H. Park et al., "Real-Time Multi-Functional Optical Coherence Tomography," Opt. Exp. 11(7), 782, (2003).

* cited by examiner

700 →

800 →

900 →

PROCESS, SYSTEM AND SOFTWARE ARRANGEMENT FOR DETERMINING AT LEAST ONE LOCATION IN A SAMPLE USING AN OPTICAL COHERENCE TOMOGRAPHY

CROSS-REFERENCE TO RELATED APPLICATION(S)

The present application claims priority from U.S. Patent Application Ser. No. 60/599,809 filed Aug. 6, 2004, the entire disclosure of which is incorporated herein by reference. This application also relates to U.S. Patent Publication No. 2002/0198457, the entire disclosure of which is incorporated herein by reference.

FIELD OF THE INVENTION

The present invention relates generally to imaging using optical coherence tomography ("OCT"), and more particularly to processes, systems and software arrangements which are capable of determining at least one location in a sample using OCT technique(s).

BACKGROUND OF THE INVENTION

Optical coherence tomography ("OCT") is an imaging technique that can measure an interference between a reference beam of light and a detected beam reflected back from a sample. A detailed system description of convention time-domain OCT has been provided in Huang et al. "Optical coherence tomography," Science 254 (5035), 1178-81 (1991). The spectral-domain variant of optical coherence tomography ("OCT"), called spectral-domain optical coherence tomography ("SD-OCT"), is a technique is a technology that is suitable for ultrahigh-resolution ophthalmic imaging. This technique has been described in Cense, B. et al., "Ultrahigh-resolution high-speed retinal imaging using spectral-domain optical coherence tomography", Optics Express, 2004 and in International Patent Publication No. WO 03/062802. In addition, U.S. patent application Ser. No. 10/272,171 filed on Oct. 16, 2002, Wojtkowski et al., "In Vivo Human Retinal Imaging by Fourier Domain Optical Coherence Tomography", Journal of Biomedical Optics, 2002, 7(3), pp. 457-463, Nassif, N. et al., "In Vivo Human Retinal Imaging by Ultrahigh-Speed Spectral Domain Optical Coherence Tomography," Optics Letters, 2004, 29(5), pp. 480-482, also relates to this subject matter. In addition, optical frequency domain interferometry ("OFDI") setup (as described in Yun, S. H. et al., "High-Speed Optical Frequency-Domain Imaging, Optics Express, 2003, 11(22), pp. 2953-2963, International Publication No. WO 03/062802 and U.S. Patent Application Ser. No. 60/514,769 filed on Oct. 27, 2004 further relate to the subject matter of the present invention.

The imaging range (e.g., a depth of the image), in SD-OCT and OFDI are generally fixed by parameters of a spectrometer. The imaging range in conventional time-domain OCT systems can be determined by the magnitude of the sweep in a reference arm length. In such systems, the overall reference arm length generally determines the position of the imaging region of a sample. By increasing the reference arm length or by moving a reference arm sweep to deeper lengths, the imaging region may be made deeper, while reducing the reference arm length can moves the imaging region to a more shallow area of the sample.

These technologies have been successfully applied to imaging biological sample. However, such biological samples may often contain irregular surfaces and structures that can make imaging problematic. For example, a curved topology of a retina generally indicates that retinal surface may appear at one depth for a particular scan, while appearing at a different depth for a scan at a different lateral location. In addition, a motion of the sample may further compounds this problem. One of the advantages of the above-referenced imaging techniques and systems employing such techniques is that they do not contact the sample and that they are non-invasive. However, this means that it is often impossible to eliminate or significantly reduce the motion of the sample relative to the imaging device. Referring to the example of retinal imaging, any slight motion on the part of the subject whose retina is being imaged would likely result in undesirable variations in position of the entire eye, in addition to the topological variations inherent in the eye itself. It should be understood that techniques to stabilize and account for motion and topological variations may significantly facilitate the application of these imaging technologies by addressing the motion problem described above.

One possible approach to address for these variations may be to increase the imaging range so as to accommodate these variations due to motion or topology. Again, using the retinal sample as an example, if the range in position of the retinal surface is 10 mm, it is possible to use a system which provides an overall imaging depth of 12 mm. With such system, the consideration for the movement of the surface from image to image are not essential since the retina would likely always be within the proper range. However, using this approach may have the effect of degrading the signal-to-noise ratio and sensitivity of the image.

Accordingly, a method to track the location of features within the sample for the purpose of determining the most appropriate imaging position and range is likely desirable. Previous techniques typically used the position of the surface of the sample as determined from a structural (intensity) image (e.g., using a cross-correlation technique or a peak signal), and provided to adapt a ranging location. (See U.S. Pat. Nos. 6,191,862 and 6,552,796). However, the detection of such prior techniques was not robust.

SUMMARY OF THE INVENTION

In contrast to the conventional techniques, an exemplary embodiment of a system, process and software arrangement according to the present invention is capable of using real time dynamic feedback to detect an axial location of features within a sample, and adjust the scan position and range accordingly. For example, an approximate location of a surface in a depth profile of an Optical Coherence Tomography scan may be located. The determination of the approximate location of the surface can be used to generate a feedback signal to, e.g., a ranging device in the reference arm. In addition, a dynamically-adjustable parameter can be used to determine the responsiveness of the feedback loop.

For example, the exemplary embodiments of the present invention, in contrast with the previously implemented systems, provide techniques for locating different types of features in the sample. These include, but are not limited to, structural (or intensity) features traditionally used in tracking techniques, as well as features of flow, birefringence, or spectroscopic data, and combinations thereof. For example, flow is described in Z. Chen et al., "Noninvasive imaging of in vivo blood flow velocity using optical Doppler tomography," Opt. Lett. 22, 1119-21 (1997), and Y. Zhao et al., "Phase-Resolved Optical Coherence Tomography and Optical Doppler Tomography for Imaging blood flow in human skin with fast scanning speed and high velocity sensitivity," Opt. Lett. 25, 114-6 (2000). The birefringence is described in J. F. de Boer et al., "Two dimensional birefringence imaging in biological tissue by polarization-sensitive optical coherence tomography," Opt. Lett. 22, 934-6 (1997). J. F. de Boer et al., "Determination of the depth-resolved Stokes parameters of light backscattered from turbid media by use of polarization-sensitive optical coherence tomography," Opt. Lett. 24, 300-2 (1999), C. E. Saxer et al., "High-speed fiber-based polarization-sensitive optical coherence tomography of in vivo human skin," Opt. Lett. 25, 1355-7 (2000), and B. H. Park et al., "Real-time multi-functional optical coherence tomography," Optics Express 11, 782 (2003). Further, the spectroscopic data is described in U. Morger et al., "Spectroscopic optical coherence tomography," Opt. Lett. 25(2), 111-3 (2000), and B. Hermann et al., "Precision of extracting absorption profiles from weakly scattering media with spectroscopic time-domain optical coherence tomography," Opt. Express 12(8), 1677-88 (2004). In addition, a reactivity parameter that affects how the evolution of these features can be used to alter system acquisition parameters e.g., (imaging location, window, range) during the acquisition.

According to one exemplary embodiment of the present invention, a system, process and software arrangement are provided to determine at least one position of at least one portion of a sample. In particular, information associated with the portion of the sample is obtained. Such portion may be associated with an interference signal that includes a first electromagnetic radiation received from the sample and a second electromagnetic radiation received from a reference. In addition, depth information and/or lateral information of the portion of the sample, may be obtained. At least one weight function can be applied to the depth information and/or the lateral information so as to generate resulting information. Further, a surface position, a lateral position and/or a depth position of the portion of the sample may be ascertained based on the resulting information.

In another exemplary embodiment of the present invention, the depth information can include (i) flow information within the at least one portion of the sample, (ii) birefringence information and polarization information associated with the at least one portion of the sample, (iii) spectroscopic information of the at least one portion of the sample, and/or (iv) intensity information of the portion of the sample. In addition, a length of the reference can be modified based on the surface position and/or the depth position. After the length is modified, the depth information and/or the lateral information may be obtained based on a new position of the reference. In addition, the length of the reference can be modified using a controllable parameter. The controllable parameter may be a responsiveness parameter which is used to dynamically control a level of modification of the length of the reference.

According to a further exemplary embodiment of the present invention, after ascertaining the particular information, at least further one of the surface position, the lateral position and/or the depth position is estimated and/or predicted as a function of the particular information. Further, the procedure can be performed a number of times to obtain a set of data associated with the particular information; and the estimation and/or prediction can be based on (or using) the set of data.

In another exemplary embodiment of the present invention, a delay arrangement can be provided which is associated with the sample and/or the reference, and facilitates variable transmissive optical paths therein. Further, at least a section of a particular path of the sample and/or the reference may be non-reciprocal. The reference can receive radiation via a path that is different from a path along which the radiation is transmitted from the reference.

According to still another exemplary embodiment of the present invention, the portion can include a feature of the sample, and the lateral position of the feature may be determined. The lateral information can include (i) flow information within the at least one portion of the sample, (ii) birefringence information and polarization information associated with the at least one portion of the sample, (iii) spectroscopic information of the at least one portion of the sample, and/or (iv) intensity information of the portion of the sample. A lateral scan range of the sample can be modified based on the lateral position. After modifying the lateral scan range, the depth information and/or the lateral information may be obtained based on a new lateral scan range. The lateral scan range may be modified using a controllable parameter (e.g., a responsiveness parameter which is used to dynamically control a level of modification of the lateral scan range).

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which.

DETAILED DESCRIPTION

Figure 1:
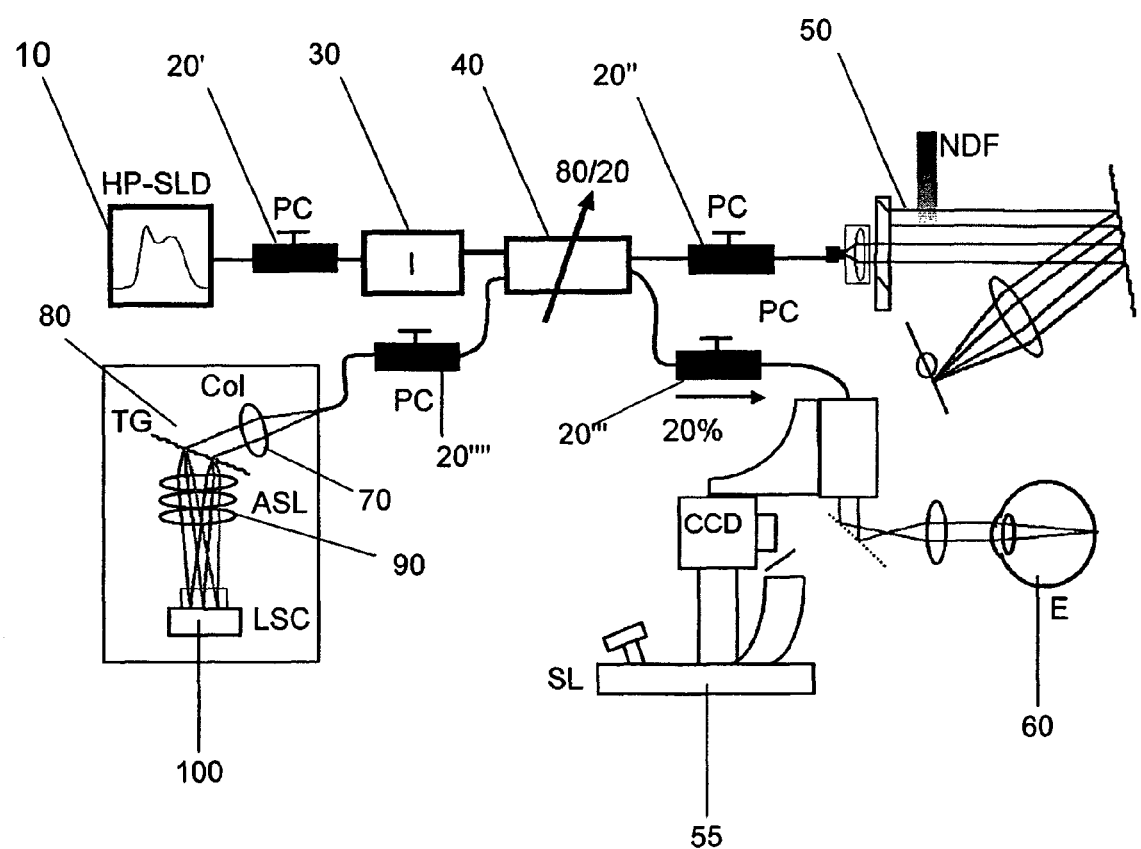
FIG. 1 is a block diagram of an exemplary embodiment of a spectral domain optical coherence tomography ("SD-OCT") arrangement according to the present invention which is capable of implementing the exemplary embodiments of the system, process and software arrangement according to the present invention.

FIG. 1 shows an exemplary embodiment of a sample configuration of a spectral domain optical coherence tomography ("SD-OCT") arrangement which can be used for implementing the exemplary embodiments of the system, process and software arrangement according to the present invention. A detailed description of operation of this arrangement is described in detail in International Patent Publication No. WO 03/062802. In particular, as shown in FIG. 1, a high-powered superluminescent diode source ("HP-SLD") 10 generates an electro-magnetic radiation or light signal which is transmitted through a first polarization controller ("PC") 20' and an optical isolator 30 so as to facilitate a one way propagation of an electro-magnetic energy to reach a signal splitter 40. The signal splitter forwards one portion of the split signal to a reference arm (which includes a second PC 20'', a reference, certain optics and a neutral density filter ("NDF") 50) and another portion of the split signal to a sample arm (which includes a third PC 20''', certain optics and a sample 60 such as the eye). Thereafter, an electromagnetic signal is reflected from the sample 60 and is combined with the light from the reference arm to form an interference signal. This interference signal is forwarded to a fourth PC 20'''', and forwarded to a collimator ("Col") 70, a transmission grating ("TG") 80, an air-spaced focusing lens ("ASL") 90, and a linescan camera ("LSC") 100 to be detected by a detecting arrangement (e.g., provided in the linescan camera), and then analyzed by a processing arrangement, e.g., a computer (not shown). Such processing arrangement is capable of implementing the various exemplary embodiments of the system, process and software arrangement according to the present invention.

Figure 2:
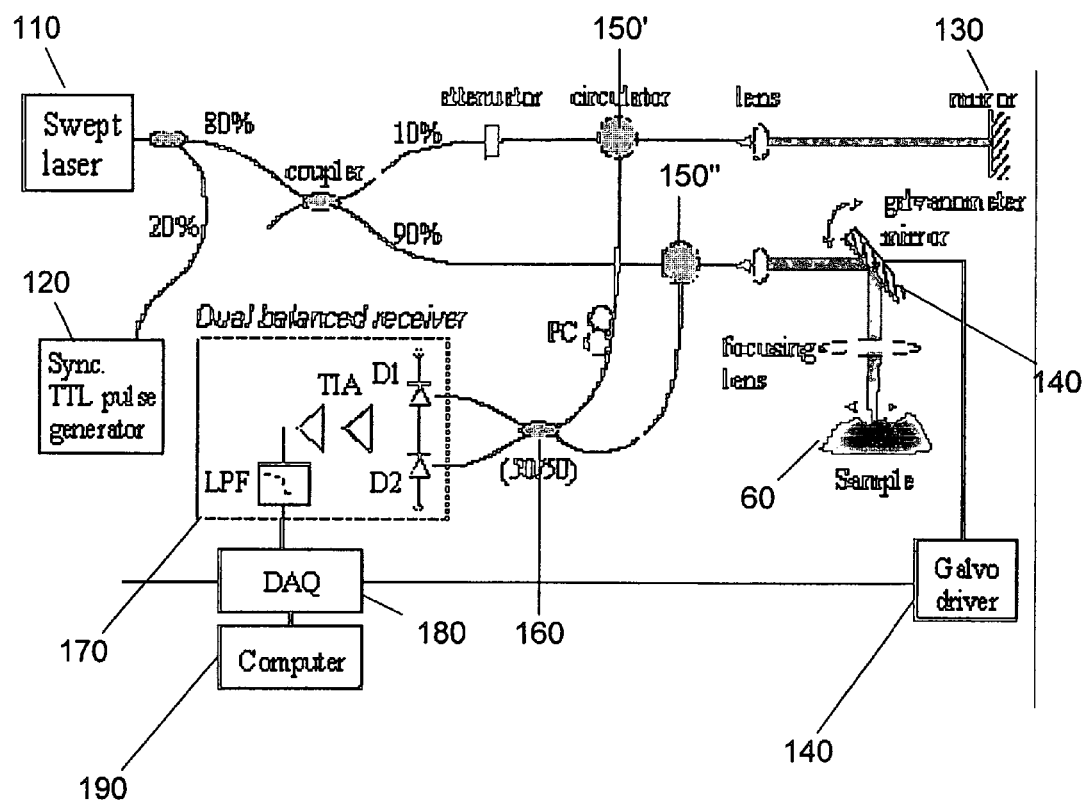
FIG. 2 is a block diagram of an exemplary embodiment of an optical frequency domain interferometry ("OFDI") arrangement according to the present invention which is capable of implementing the exemplary embodiments of the system, process and software arrangement according to the present invention.

FIG. 2 shows an exemplary embodiment of an optical imaging frequency domain intereferometry ("OFDI") arrangement according to the present invention which is capable of implementing the exemplary embodiments of the system, process and software arrangement according to the present invention. A detailed description of various embodiments of the OFDI arrangement is provided in U.S. Patent Application Ser. No. 60/514,769. For example, the light source may be a wavelength-swept source 110. In order to generate a synchronization signal, a portion of the laser output (for example—20%) is obtained, and detected using a fast InGaAs photo-detector through a narrowband fixed-wavelength filter. The detector generates a pulse when the output spectrum of the laser sweeps through the narrow passband of the filter. The detector pulse is fed to a digital circuit 120, e.g., a synchronous TTL pulse generator, for converting the resultant signal to a TTL pulse train. The TTL pulses are used to generate gating pulses for signal sampling. 90% of the remaining light is directed to the sample arm and 10% to the reference mirror 130. This exemplary arrangement can utilize an optical probe based on a galvanometer mirror (e.g., scanner) 140 and an imaging lens. The galvanometer-mounted mirror 140 is controlled by a glava-driver 145 so as to scan the probe light transversely on the sample 60. The total optical power illuminated on the sample 60 may be approximately 3.5 mW. The light reflected from the reference mirror 130 and the sample 60 is received through magneto-optic circulators 150', 150'', and combined by a 50/50 coupler 160. A fiber-optic polarization controller may be used in the reference arm to align polarization states of the reference and sample arms.

In general, a relative intensity noise ("RIN") of the received light signal may be proportional to a reciprocal of the linewidth, and the relatively high RIN can be reduced by dual balanced detection (e.g., using a dual balanced receiver 170). The differential current of two InGaAs detectors D1 and D2 in the receiver 170 may be amplified using trans-impedance amplifiers ("TIA") having a total gain of 56 dB, and passed through a low pass filter ("LPF") with a 3-dB cutoff frequency at approximately half the sampling rate. The common-noise rejection efficiency of the receiver 170 may be typically greater than 20 dB. In addition to the RIN reduction, the balanced detection may provide other significant benefits—a suppression of a self-interference noise originating from multiple reflections within the sample and optical components; an improvement in the dynamic range; and a reduction of a fixed-pattern noise by greatly reducing the strong background signal from the reference light. Thereafter, a detecting arrangement 180 receives such signals, and forward them to a processing arrangement 190 (e.g., a computer) which implements the exemplary embodiments of the system, process and software arrangement according to the present invention to reduce dispersion, and assist in displaying a resultant image that is based on the original image and the reduction of the dispersion.

Both of these exemplary arrangements, e.g., the SD-OCT arrangement described above with reference to FIG. 1 and the OFDI arrangement described above with reference to FIG. 2, are capable of using real time dynamic feedback to detect an axial location of features within a sample, and adjust the scan position and range accordingly. For example, an approximate location of a surface in a depth profile of the OCT scan may be located. The determination of the approximate location of the surface can be used to generate a feedback signal to, e.g., a ranging device in the reference arm of these systems. In addition, a dynamically-adjustable parameter can be used by these exemplary systems to determine the responsiveness of the feedback loop.

Figure 3:
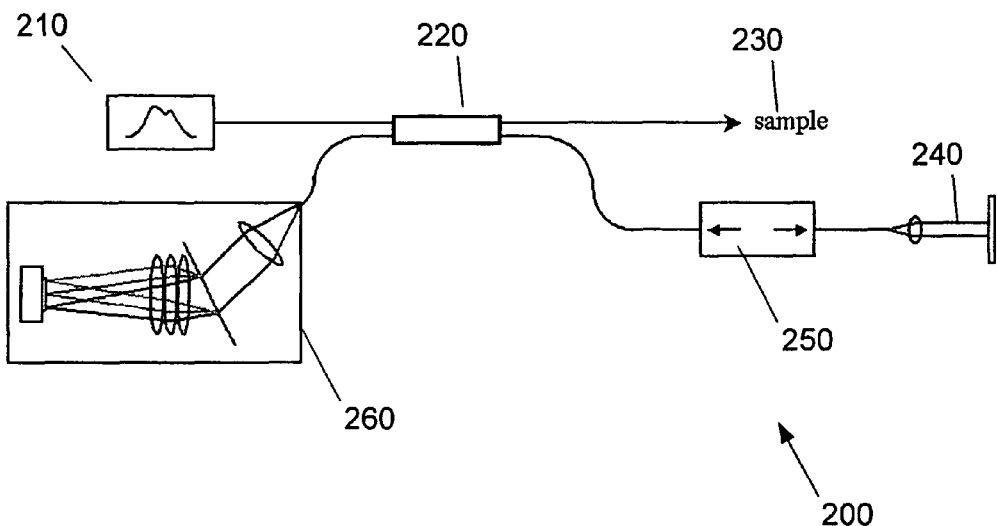
FIG. 3 is a high level diagram of another exemplary SD-OCT system that includes a transmissive delay line and a broadband source coupled into a splitter, which is capable of implementing the exemplary embodiments of the system, process and software arrangement according to the present invention.

FIG. 3 shows a high level diagram of another exemplary SD-OCT system 200 that includes a transmissive delay line and a broadband source coupled into a splitter, which is capable of implementing the exemplary embodiments of the system, process and software arrangement according to the present invention. In particular, the exemplary system of FIG. 3 illustrates a broadband source 210 (e.g., a high-powered superluminescent diode) is coupled to a fiber splitter 220, which may have the particular splitting ratios (e.g., 50/50, 80/20, 90/10 or 99/1). One portion of the split signal is transmitted from the splitter 220 to a sample 230, and the other portion of the split signal is transmitted from the splitter 220 to a reference arm. The exemplary reference arm can include a stationary mirror 240 and a variable length transmissive delay arrangement 250. Such configuration of the reference arm in this exemplary embodiment can be differentiated from a delay line in which the overall reference optical path length is generally controlled by moving the mirror itself. The light signal returning from both the sample arm 230 and the reference arm (240, 250) interfere upon their return path through the splitter 220, and are detected with a spectrometer 260 as described above.

Figure 4:
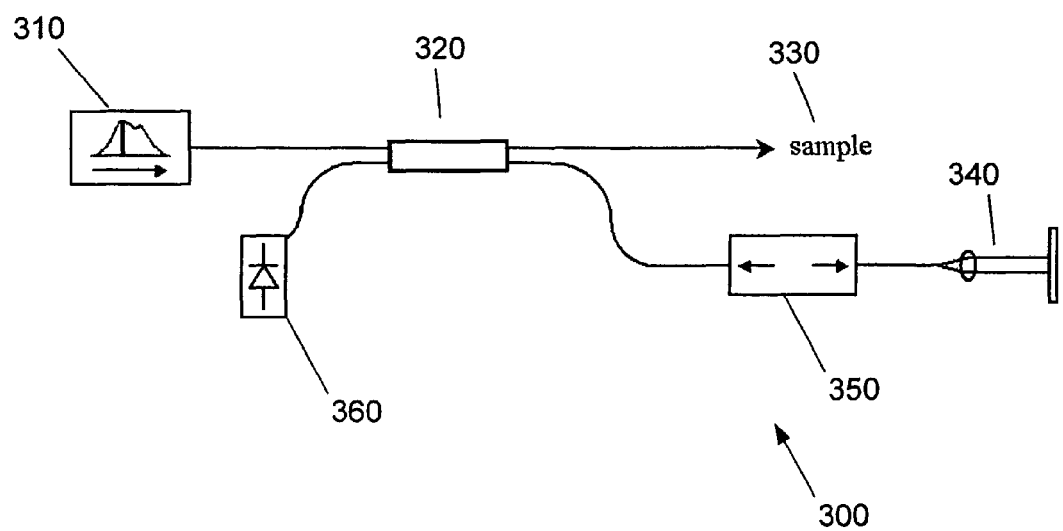
FIG. 4 is a high level diagram of another exemplary OFDI system that includes a transmissive delay line and a swept source coupled into a splitter, which is capable of implementing the exemplary embodiments of the system, process and software arrangement according to the present invention.

FIG. 4 shows a high level diagram of another exemplary OFDI system 300 that includes a transmissive delay line and a swept source coupled into a splitter, which is capable of implementing the exemplary embodiments of the system, process and software arrangement according to the present invention. In particular, the exemplary system of FIG. 4 illustrates a swept source 310 is coupled to a fiber splitter 320, which is similar to the splitter 220 may have the particular splitting ratios (e.g., 50/50, 80/20, 90/10 or 99/1). Similarly to the description of the system shown in FIG. 3, one portion of the split signal is transmitted from the splitter 320 to a sample 330, and the other portion of the split signal is transmitted from the splitter 320 to a reference arm. Again, the exemplary reference arm can include a stationary mirror 340 and a variable length transmissive delay arrangement 350. The light signal returning from both the sample arm 330 and the reference arm (340, 350) interfere upon their return path through the splitter 320. However, in contrast with the system shown in FIG. 3, the system of FIG. 4 includes a photodiode 360 which is used for the detection of the interfered signal.

Figure 5:
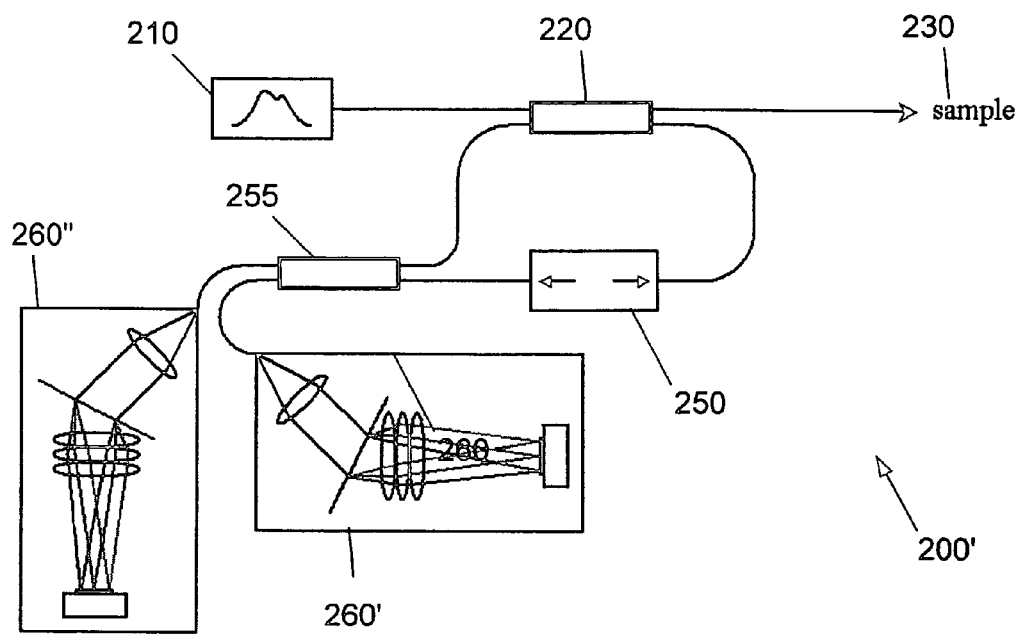
FIG. 5 is a high level diagram of yet another exemplary SD-OCT system that excludes a mirror in the transmissive reference arm, which is coupled to one of two splitter, and which is capable of implementing the exemplary embodiments of the system, process and software arrangement according to the present invention.

FIG. 5 shows a high level diagram of yet another exemplary SD-OCT system 200', which is capable of implementing the exemplary embodiments of the system, process and software arrangement according to the present invention. In the this exemplary embodiment, the transmissive reference arm excludes the mirror. However, the splitter 220 as shown in FIG. 5 is coupled to another splitter 255, as well as to the transmissive delay arrangement 250. In addition, the light is reflected back from the sample 230 and the reference arm and light the second splitter 255 which splits the signal and forward the split portions of the reflected signal to two separate spectrometers 260', 260", respectively.

Figure 6:
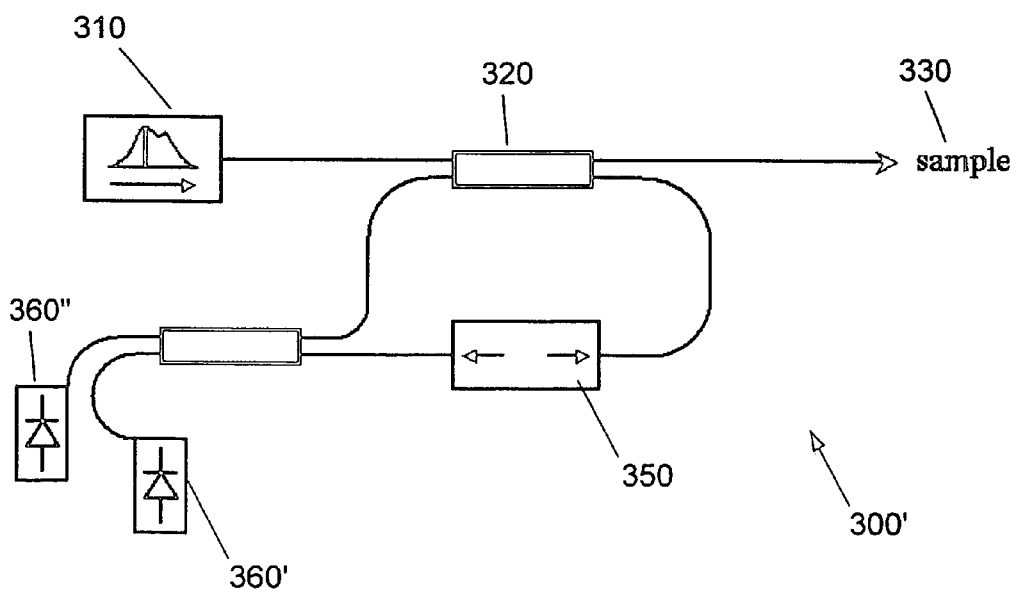
FIG. 6 is a high level diagram of yet another exemplary OFDI system that excludes a mirror in the transmissive reference arm, which is coupled to one of two splitter, and which is capable of implementing the exemplary embodiments of the system, process and software arrangement according to the present invention.

FIG. 6 shows a high level diagram of yet another exemplary OFDI system 300' that has similar changes as illustrated in FIG. 5. Indeed, the transmissive reference arm excludes the mirror, and other splitter 355 to receive the reflected signal from the first splitter 320 and from the transmissive delay arrangement 350. In addition, two separate diodes 360', 360" are provided to detect the split signals from the second splitter 355.

Figure 7:
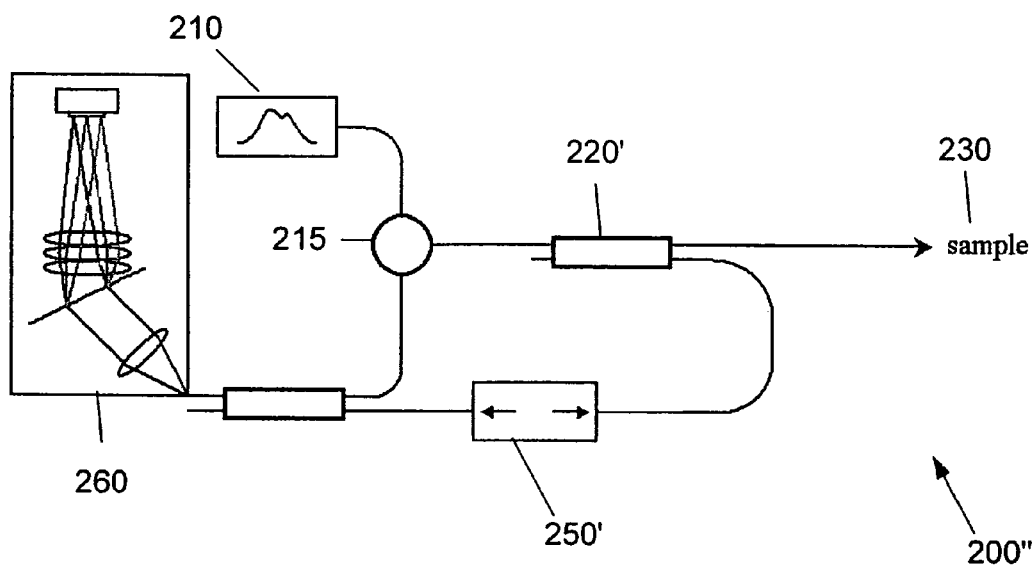
FIG. 7 is a high level diagram of yet another exemplary SD-OCT system similar to that of FIG. 5, except that a circulator is provided between the source and the first splitter, and which is capable of implementing the exemplary embodiments of the system, process and software arrangement according to the present invention.
Figure 8:
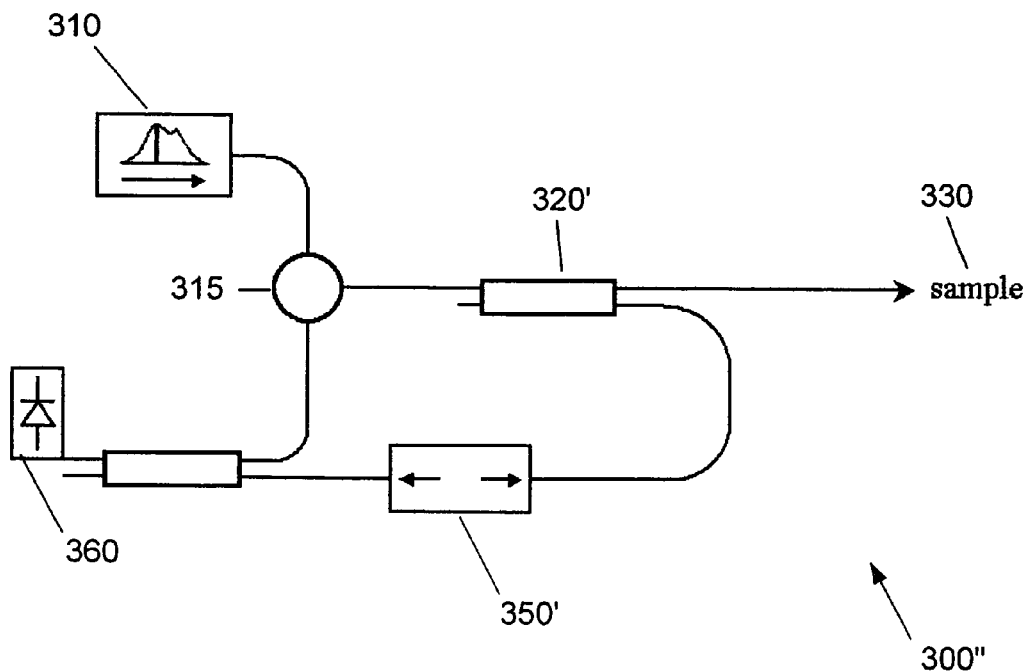
FIG. 8 is a high level diagram of yet another exemplary OFDI system similar to that of FIG. 6, except that a circulator is provided between the source and the first splitter, and which is capable of implementing the exemplary embodiments of the system, process and software arrangement according to the present invention.

FIGS. 7 and 8 show high level diagrams of still further another exemplary systems 200'', 300'', i.e. SD-OCT and OFDI, respectively, that are similar to those of FIGS. 5 and 6. The main difference between the exemplary embodiments shown in FIGS. 7 and 8 and those illustrated in FIGS. 5 and 6 is the presence of a circulator 215, 315 in the systems of FIGS. 7 and 8 coupled between the source 210, 310 and the first splitter 220, 320, respectively. This will affect the choice of splitting ratios used in the respective first splitters 220, 320 depending on the application. For example, when using such systems to image the biological tissue, where sample reflectivity is typically very low, the use of the configuration of the systems shown in FIGS. 7 and 8 (with the splitters 220, 230 with the ratios of 90/10 or 99/1) may be preferable so as to detect more of the light returning from the sample 230, 330. The use of such splitting ratios for the configurations of the systems shown in FIGS. 5 and 6 would likely result in a detection of a significantly smaller proportion of the light returning from the sample 23, 330. In addition, the systems of FIGS. 7 and 8 have one detection arrangement (i.e., the spectrometer 260 and the diode 360).

Figure 9:
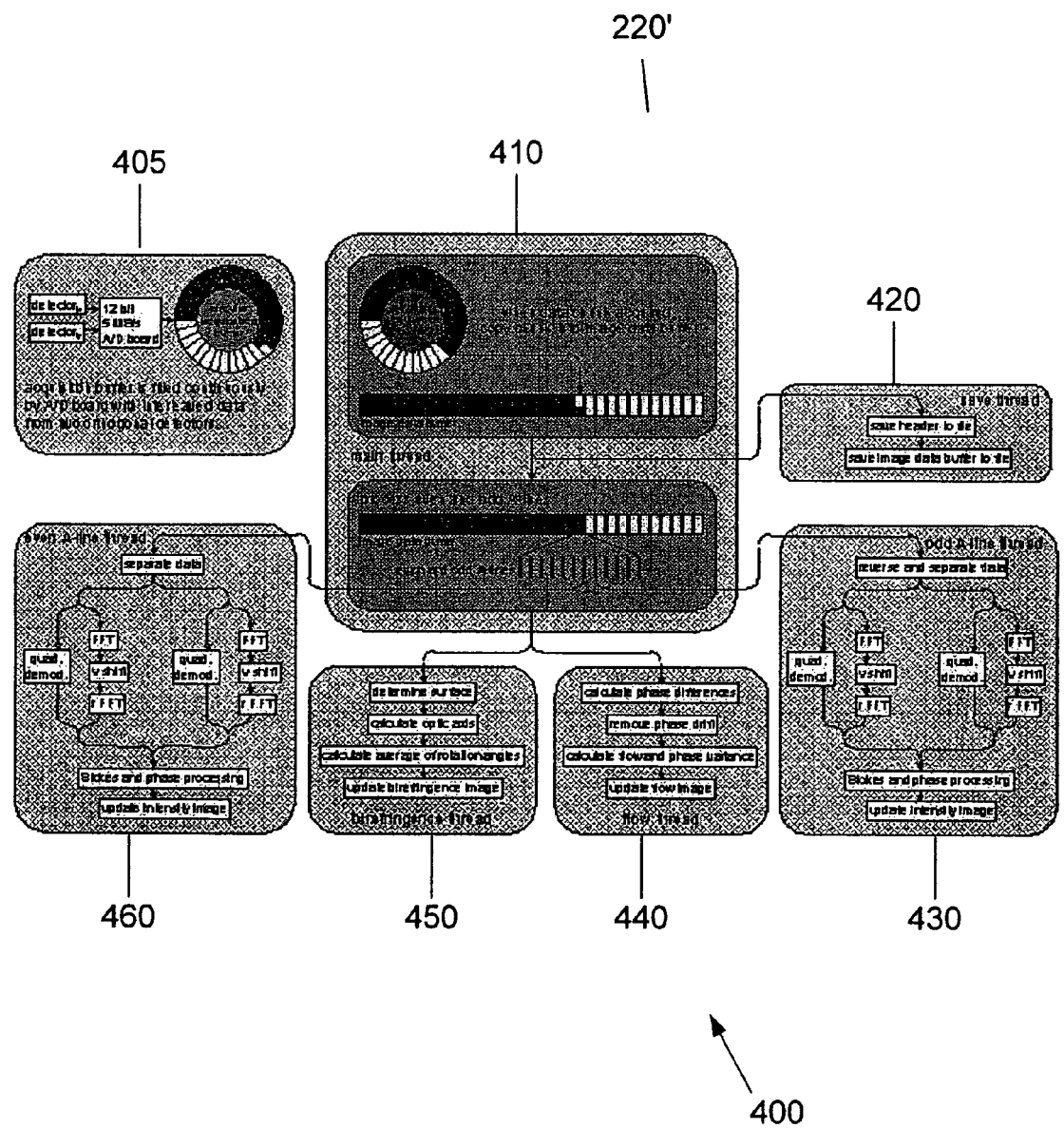
FIG. 9 is a flow diagram of an exemplary embodiment of a real-time polarization-sensitive data acquisition and processing software according to the present invention, which is capable of implementing the exemplary embodiments of the system, process and software arrangement according to the present invention.
Figure 9A:
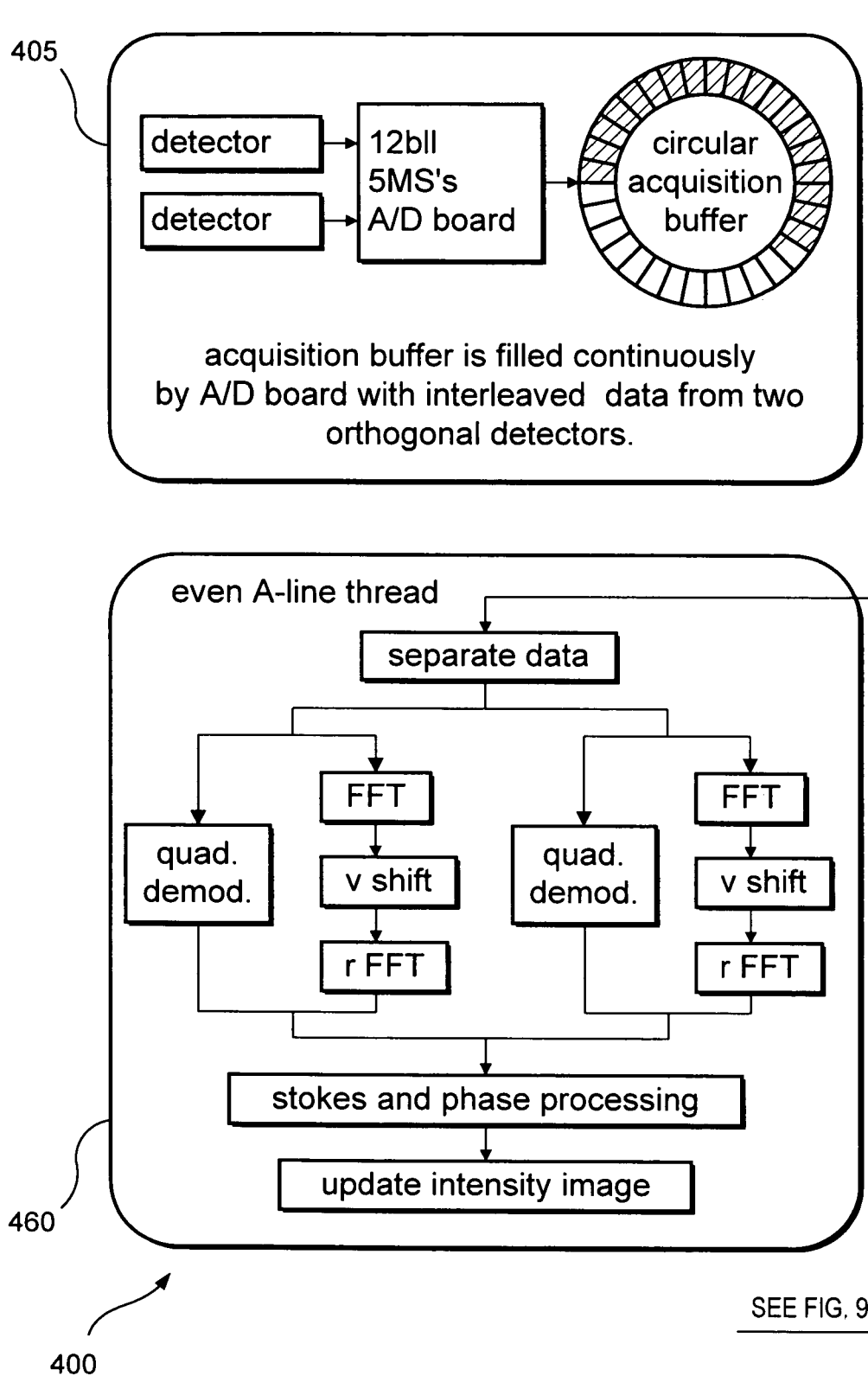
Figure 9B:
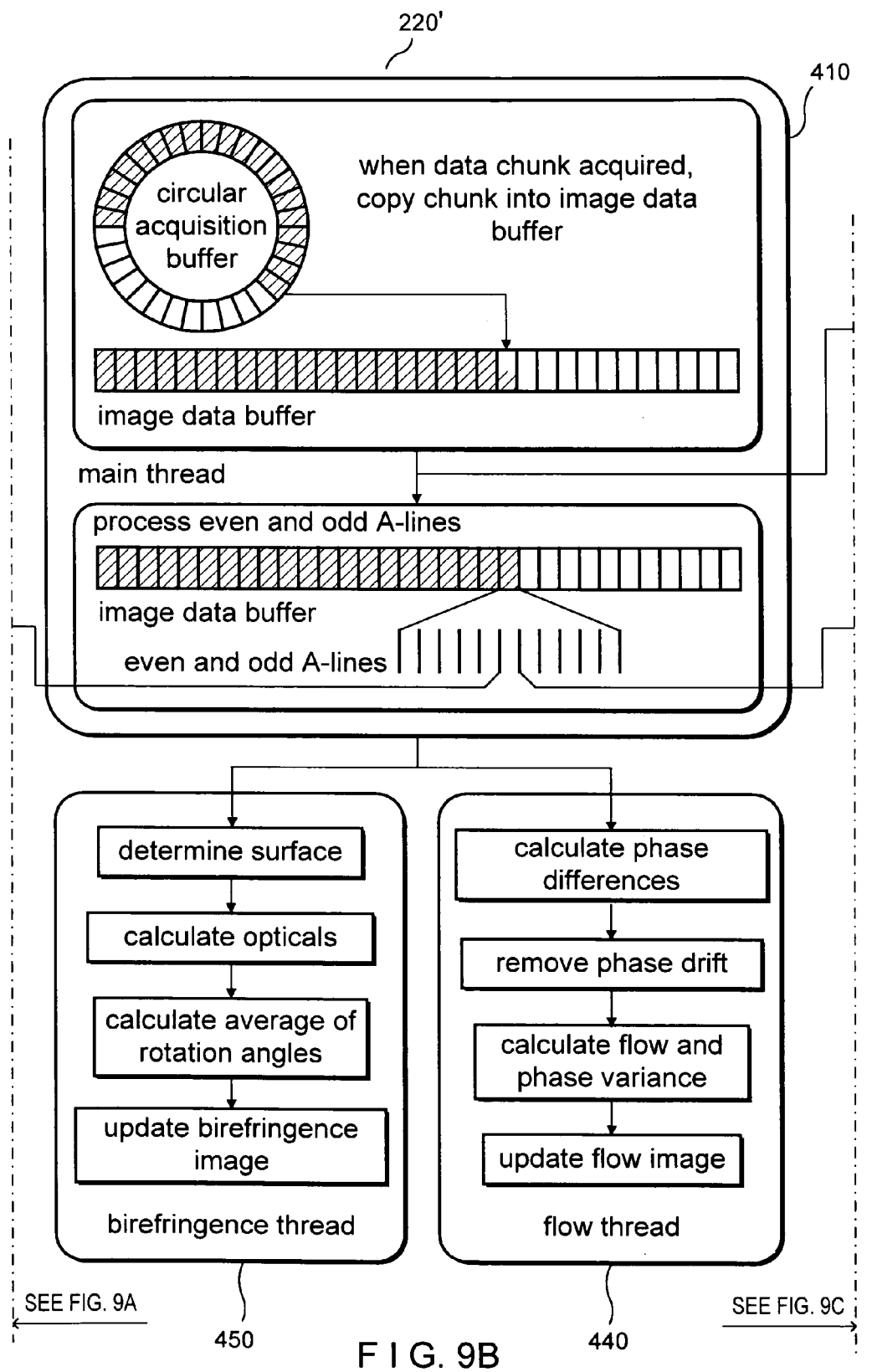
Figure 9C:
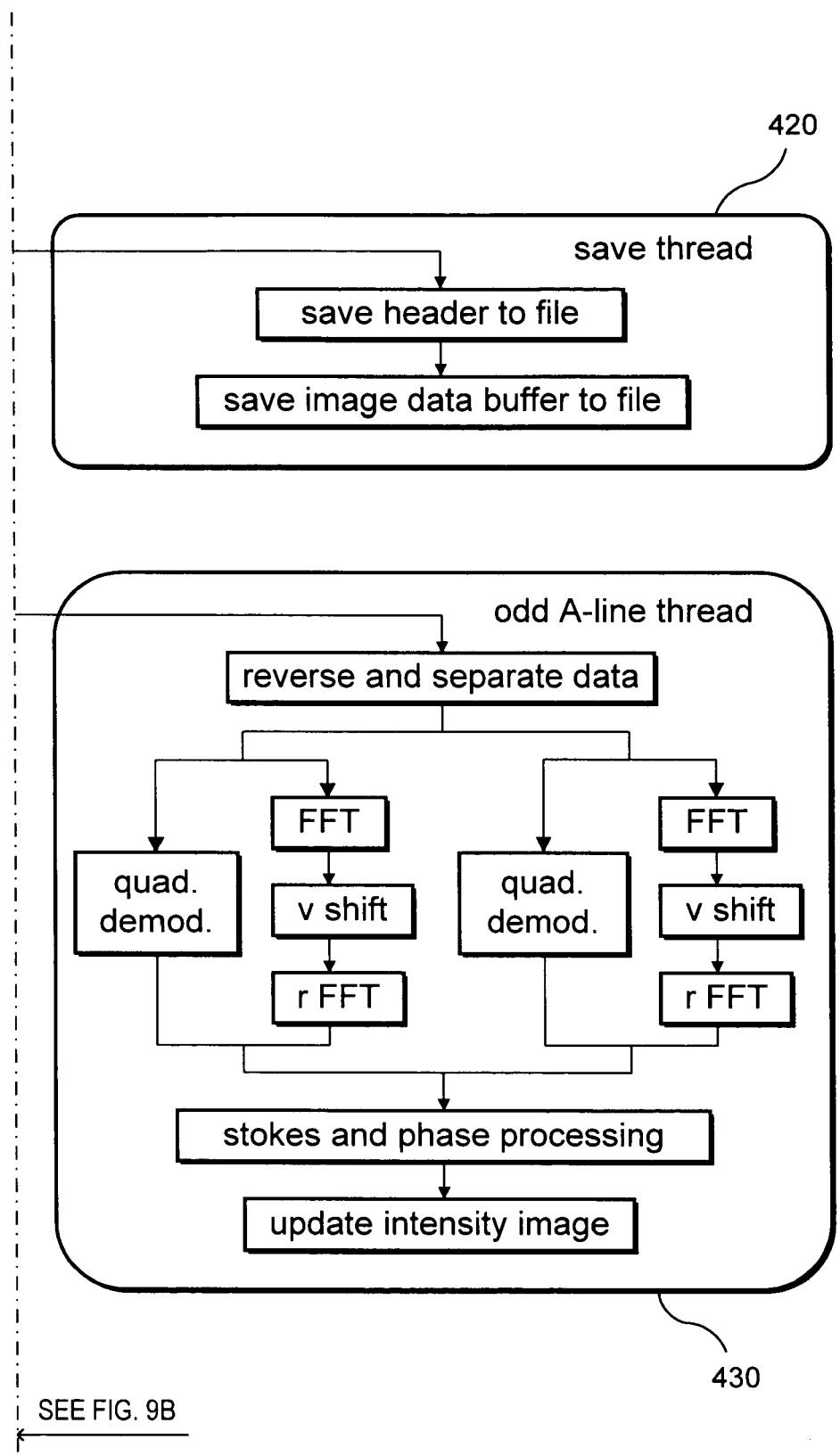

FIG. 9 shows a flow diagram of an exemplary embodiment of a real-time polarization-sensitive data acquisition and processing software 400 according to the present invention, which is capable of implementing the exemplary embodiments of the system, process and software arrangement according to the present invention. For example, the exemplary software begins a main thread by acquiring a chunk of data 405, which is them processed 410 as soon as it is acquired. This procedure may include an activation of even and odd A-line processing threads 460, 430, respectively to convert the detected interference patterns into Stokes parameters and phase information, as well as updating the intensity image. When the initial processing of the data has been completed, the birefringence and flow threads 450, 440, respectively can perform their respective analysis and image updates. The save thread 420 can writes raw data to a disk once the image is completely acquired.

Figure 10:
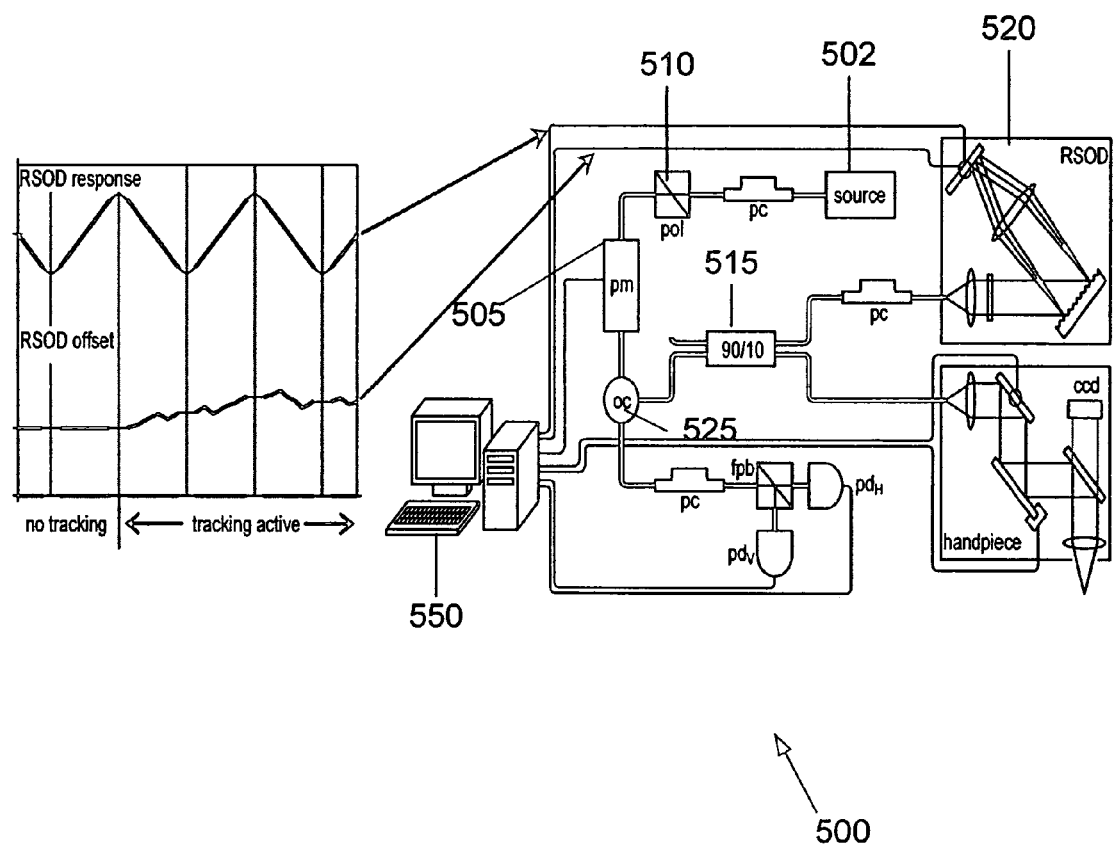
FIG. 10 is a system diagram of an exemplary embodiment of a polarization-sensitive OCT ("PS-OCT") system (and waveforms used for the signals generated by the source), which is capable of implementing the exemplary embodiments of the system, process and software arrangement according to the present invention.

FIG. 10 is a system diagram of an exemplary embodiment of a polarization-sensitive OCT ("PS-OCT") system 500 (and waveforms used for the signals generated by the source), which is capable of implementing the exemplary embodiments of the system, process and software arrangement according to the present invention. For example, a low-coherence source 502 (e.g., AFC BBS1310) with a center wavelength of 1310 nm, a FWHM bandwidth of 70 nm, and total output power of 9 mW was linearly polarized may be used in this system such that equal-magnitude wave components are aligned parallel and perpendicular to the optic axis of an electro-optic polarization modulator 505. Light is coupled through a standard single-mode fiber to a polarization-independent optical circulator 510, and then divided by a fiber optic splitter 515 in a 90/10 ratio into sample and reference arms.

For example, 2.5 mW of source light may be incident onto the surface of the sample in a focused spot of, e.g., 30-mm diameter. A grating-based rapid scanning optical delay line 520 ("RSOD") can be used with the source spectrum offset on the scanning mirror to provide both group and phase delay scanning so as to generating a carrier frequency at about 800 kHz. A two-step voltage function may be used to drive the polarization modulator 505 such that it is synchronized with the 1-kHz triangular scanning waveform of the RSOD 520, such that the polarization states that are incident upon the sample during inward and outward A-line scans can be orthogonal in the Poincaré sphere representation. A polarizing cube can be inserted into the reference arm to ensure that light in the RSOD 520 is provided in substantially the same linear state, regardless of the polarization state at the sample. Static polarization controllers in the detection and reference arms may be aligned for an equal distribution of the reference arm light over both the horizontal and vertical detection channels for both input polarization states. Electronic signals from each detector can be amplified, filtered and digitized with a 12-bit 5-Msample_s analog-to-digital board (e.g., National Instruments NI 6110).

The exemplary techniques that are described herein below (e.g., adaptive ranging techniques) according to the present invention can be implemented using the exemplary systems described above with reference to FIGS. 1-9, as well as other systems which are within the scope of the present invention, and with those systems that are known and understood to those having ordinary skill in the art. For example, a processing arrangement (e.g., the computer 190, 550 of FIGS. 2 and 9, respectively) may be used to a control waveform output to various components of the system as well as acquiring data from the detector arm of the interferometer. This technique is described in B. H. Park et al., "Real-Time Multi-Functional Optical Coherence Tomography," Opt. Exp. 11(7), 782 (2003). The rapid scanning optical delay line (RSOD) as described above and discussed in G. J. Tearney et al., "High-Speed Phase- and Group-Delay Scanning with a Grating-Based Phase Control Delay Line," Opt. Lett. 22(23), 1811 (1997) in the reference arm can be controlled by the sum of, e.g., two functions: (i) a triangular wave with an amplitude and frequency related to the depth range and scan rate, and (ii) an offset voltage that shifts the depth range. A single image can be divided into data chunks, each consisting of a small number, D, of consecutive depth scans of length N points.

A position function, e.g., a weighted first moment, may be calculated according to the following:

$$P = \frac{\sum_{d=1}^{D} \sum_{n=1}^{N} n W_{d,n}}{\sum_{d=1}^{D} \sum_{n=1}^{N} W_{d,n}} \tag{1}$$

where d and n is a depth scan and point within the depth scan, respectively, and thus $W_{d,n}$ represents a weight for a particular position in the image. For example, this weight may be equal to the reflected light intensity on either a linear or logarithmic scale, depending on user preference during software initialization. In most cases, using the logarithm of the intensity gives more intuitive results, as the intensity image itself is shown on a logarithmic scale as well.

Figure 12:
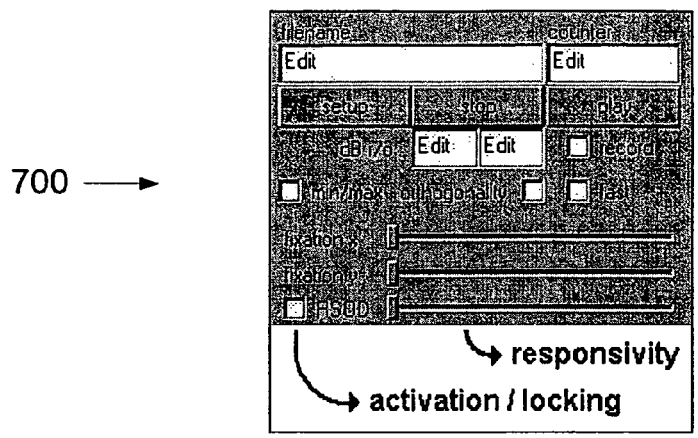
FIG. 12 is an exemplary illustration of a software interface which operates with the system, process and software arrangement according to the present invention which includes adaptive ranging activation/locking checkmark control and responsivity slide bar control.

An exemplary graphic user interface 700 according to the present invention with can be used with this technique during acquisition has two controls related to adaptive ranging, as shown in FIG. 12. For example, the RSOD offset voltage, $V_{offset}$, can be initially set to zero. When the activation/locking checkmark control is activated, the software may store the most current first moment as a separate variable, PL. The slide bar control determines a responsivity parameter, R. For each subsequent data chunk, a change in offset voltage, $\Delta V_{offset}$, may be determined by the product of the responsivity, R, and the difference between the calculated first moment for the current data chunk, P, and the locking value, $P_L$, as provided by:

$$\Delta V_{offset} = -R \cdot (P - P_L) \tag{2}$$

This value can be added to the offset voltage, and the updated value may be transmitted to the RSOD between the acquisition of the data chunks. Equation (2) is similar to Hooke's law governing a spring, where R can be equated to a spring constant. The fact that R can be dynamically controlled during acquisition then allows for a determination of the appropriate parameters for optimal damping of patient movement. The ranging procedure continues for each data chunk until the check mark control is deactivated, and the software relocks on to a new position when it is activated again.

It should be understood that the above description is merely an exemplary implementation of an exemplary embodiment of the technique according to the present invention. On having ordinary skill in the are can easily modify and customize it according to the concepts described herein. For example, depending on the application, it is possible to constantly (e.g., periodically) update the scanning range within an image. Alternatively or in addition, it may be beneficial to only update the position between images or between sets of images. These exemplary variations can be easily accomplished by altering the size of the data chunk to be anywhere from a single depth profile, to a particular fraction of an image, to several images.

As described above, the weight function can be based on the reflected intensity on either a linear or logarithmic scale, depending on the type of tissue being scanned. A wide array of other functions based on intensity can also be used, such as, e.g., an exponential, a (fractional) power of the intensity or a higher order polynomial could be used to enhance weakly reflecting features that use tracking. Indeed, it may be beneficial for certain situations to base the weight function on something entirely different. Various extensions of OCT, such as polarization-sensitive OCT ("PS-OCT") and optical Doppler tomography ("ODT"), can enhance contrast by providing images of phase retardation and flow, respectively.

Multi-functional techniques that are capable of measuring intensity, flow, the full gamut of polarization properties, and even spectroscopy of a sample have also been demonstrated. It is also possible to base the above-described weighting function on any of such features. For example, it is possible to base the weight function on a flow if it is particularly important to track the location of blood vessels. The flexibility in the type of weighting function can even allow us to combine the various types of data at our disposal. A weight that is a combination of some function involving flow and some other function involving phase retardation may allow for the tracking of vessels surrounded by a muscular sheath. The fact that different mathematical functions can be used further enables for an emphasis or de-emphasis of certain information as. For example, it is possible to use a combination of spectroscopic data and flow, with an emphasis on the latter, so as to distinguish and lock on blood containing certain features, and would preferentially focus on those with a flow component.

The position function, P, can also be configured to the type of tissue being analyzed. For example, it is possible to focus the tracking on the position of superficial or deeper structures by changing to what power the depth, n, of a point is raised, e.g., $$P = \frac{\sum_{d=1}^{D} \sum_{n=1}^{N} n^x W_{d,n}}{\sum_{d=1}^{D} \sum_{n=1}^{N} W_{d,n}}. \tag{3}$$

Increasing x can put more emphasis on deeper structures of interest whereas decreasing x would emphasize more superficial layers. Alternatively, it is possible to utilize linear combinations of higher order moments, e.g., using the second moment of position combined with a weight based on flow could track the location of a changing flow profile. Another potentially useful application is with tracking locations where features might have phase wrapping. Some examples of this are with flow determined by phase shifts or birefringence as determined by cumulative phase retardation. In both these cases, the mere presence of the source of contrast can potentially be misleading and only by observing their spatial distribution can we ascertain a more accurate description of the tissue. It can easily be seen that the combination of position and weight functions can be adapted to track the location of a wide variety of features, both in terms of their inherent properties (intensity, phase retardation, flow, etc.) and in terms of their spatial properties.

Figure 13:
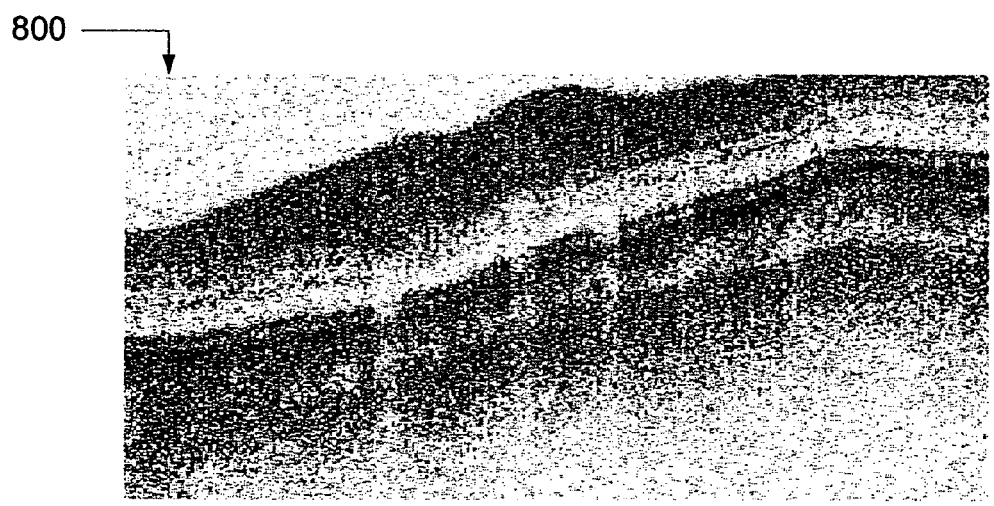
FIG. 13 is an exemplary image of a portion of a retina acquired using a technique without tracking.
Figure 14:
FIG. 14 is an exemplary image of a portion of a retina acquired using motion tracking according to an exemplary embodiment of the present invention.

Further, the nature of the feedback loop can be configured to a particular application as well. One way of visualizing the feedback loop can be as a potential well. Equation (2) described above can be equated to Hooke's law governing the motion of a spring, which acts a quadratic potential well. Altering the responsivity parameter generally alters the width of the well, and enable a quick correction for under- or over-damping of motion artifact. It is also possible to modify the nature of the potential well itself, e.g., creating a square well or using another function based on the difference between the current position as the locked position. Indeed, it is possible to use higher order polynomials of not only the difference in position, but also the derivatives of the position as well to design the feedback loop to respond to velocity or acceleration of the tissue in question. Further, instead of using such functions to modify the change in offset voltage, the functions can modify other statistic of the offset voltage such as acceleration. In addition, a locking scheme can be used where the exemplary technique according to the present invention may lock on to a tissue displacement in response to acoustic, photothermal or other external stimuli to the tissue. FIG. 13 shows an exemplary image 800 of a portion of a retina acquired using a technique without tracking. The benefits of the present invention can be ascertained by reviewing an image 900 illustrated in FIG. 14 which corresponds to the of the retina displayed in the image 800 of FIG. 13. However, the image 900 of FIG. 14 was acquired using motion tracking according to an exemplary embodiment of the present invention.

Another manner of visualizing the effect of the dynamic responsivity parameter is that the user can use such parameter to control how the system reacts to and anticipates any changes in the position of features being imaged. The example of the usefulness of such exemplary feature is as follows: assume a feature is moving at a constant velocity. An autoranging procedure that merely takes the position from time point to time point will likely be at least slightly behind the true position of an object. This is due to the time the procedure has reacted to a specific position, and thus the object will likely have already moved to a new one. Using the exemplary reactivity parameter in accordance with the present invention, the system can overcompensate for the difference between the current and locked positions, and thus predict where the feature of interest would likely appear. Due to the fact that this is a dynamically controllable parameter, the user may use it to quickly tailor the response to fit the imaging subject.

The exemplary tracking technique according to the present invention described above is not limited to axial degrees of freedom. By providing a feedback loop to the lateral motion controllers, e.g., an x-y galvo set, the exemplary tracking technique can also provide a transversal lock on blood vessels or other structures that can be distinguished through their structure, polarization properties or velocity through, e.g., a Doppler shift. Similar feedback loops can be applied for controlling the range of the image by tracking the boundaries of the region of interest.

Figure 11:
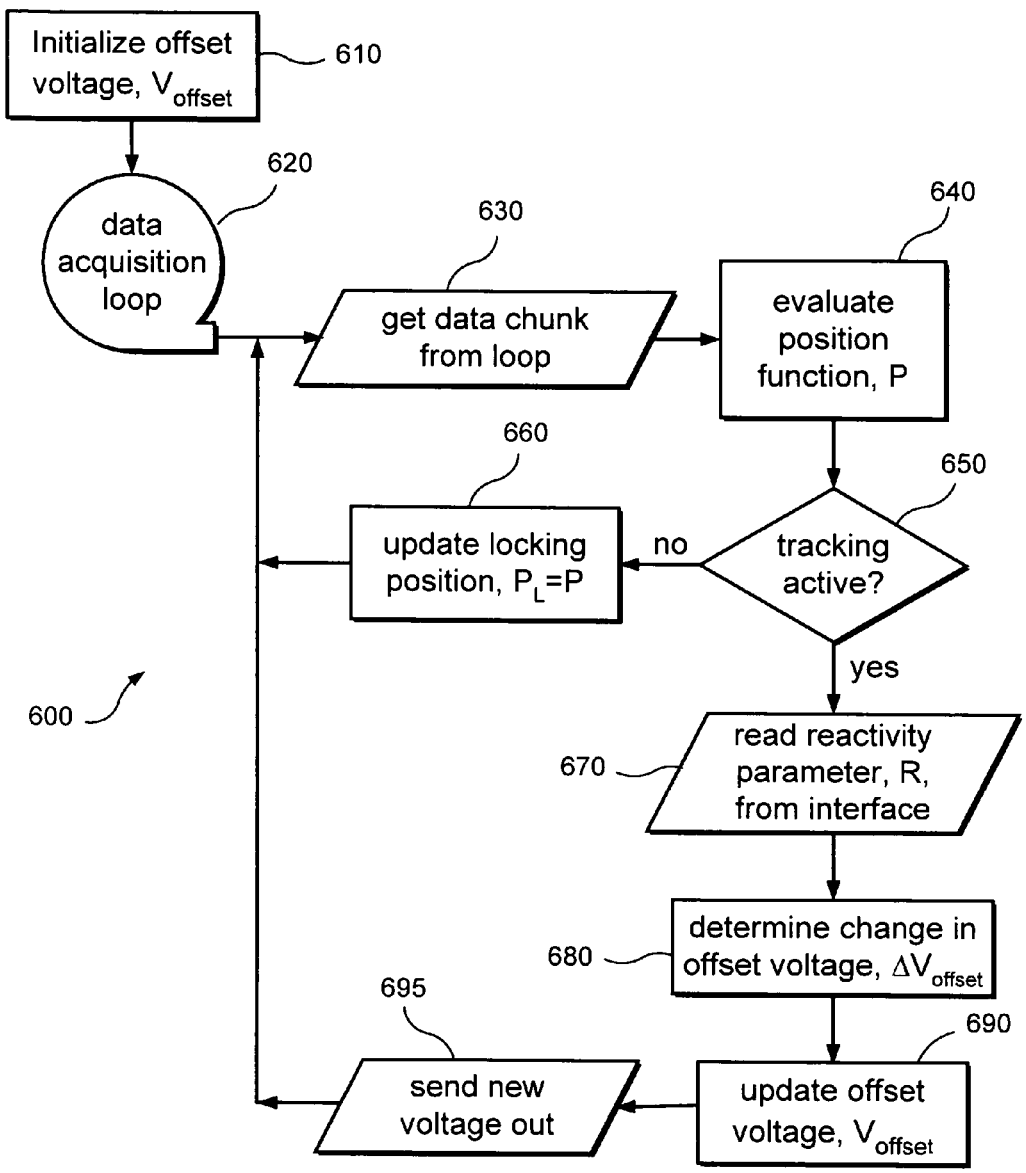
FIG. 11 is a flow chart of an exemplary embodiment of a method according to the present invention which implements a tracking technique that uses a dynamic responsivity parameter.

FIG. 11 is a flow chart of an exemplary embodiment of a method according to the present invention which implements a tracking technique that uses a dynamic responsivity parameter. This exemplary technique can be implemented using the exemplary systems shown in FIGS. 1-8, and described herein. In particular, the RSOD offset voltage is initially set to 0 in step 610, and a continuous data acquisition loop is started in step 620. A position function, P, can then be evaluated for each newly acquired data chunk. For example, the data chunk may be obtained from the loop in step 630. For example, the data chunk acquisition provided in step 630 can be obtained from blocks 410-460 as shown in FIG. 9.

Then, the position function, P, can be evaluated in step 640. If tracking is not active, then the program updates the value of a locking position PL in step 660. Otherwise, the procedure is continued to step 670 in which a reactivity/reaction parameter, R, is obtained from the interface. One of the goals of the tracking procedure, when activated, is to maintain the position of the most recently acquired data chunk as close to this locking value as possible. This is done by determining the change in the RSOD offset voltage most appropriate for the given value of the responsivity in step 680, and offset voltage, $V_{offset}$, is updated in step 690. Finally, the new voltage is transmitted in step 695, and the process returns to step 630. Thus, this exemplary technique facilitates the most current evaluation of the position function.

The foregoing merely illustrates the principles of the invention. Various modifications and alterations to the described embodiments will be apparent to those skilled in the art in view of the teachings herein. For example, the invention described herein is usable with the exemplary methods, systems and apparatus described in U.S. patent application Ser. No. 60/514,769. It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced above are incorporated herein by reference in their entireties.

The invention claimed is:

1. A system to determine at least one position of at least one portion of a sample, comprising:
a computer processing arrangement which obtains information associated with the at least one portion of the sample, the at least one portion being associated with an interference signal that includes a first electro-magnetic radiation received from the sample and a second electro-magnetic radiation received from a reference, wherein the computer processing arrangement further:
I. obtains at least one of depth information or lateral information of the at least one portion of the sample,
II. applies at least one weight function to the at least one of the depth information or the lateral information so as to generate resulting information,
III. ascertains a particular information which is at least one of a surface position, a lateral position or a depth position of the at least one portion of the sample based on the resulting information, and
IIIA. modifies a length of the reference based on the particular information.

2. The system according to claim 1, wherein at least one of the depth information or the lateral information includes flow information within the at least one portion of the sample.

3. The system according to claim 1, wherein at least one of the depth information or the lateral information includes at least one of birefringence information and polarization information associated with the at least one portion of the sample.

4. The system according to claim 1, wherein at least one of the depth information or the lateral information includes spectroscopic information of the at least one portion of the sample.

5. The system according to claim 1, wherein, after ascertaining the particular information, the processing arrangement:
   IV. at least one of estimates or predicts at least one of the surface position, the lateral position and the depth position as a function of the particular information.

6. The system according to claim 5, wherein the processing arrangement:
   V. performs at least one of procedures (I)-(IIIA) to obtain a set of data associated with the particular information; and
   VI. performs procedure (IV) based on the set of data.

7. The system according to claim 1, wherein at least one of the depth information or the lateral information includes intensity information of the at least one portion of the sample.

8. The system according to claim 1, further comprising a delay arrangement associated with at least one of the sample and the reference, and which facilitates variable transmissive optical paths therein.

9. The system according to claim 1, wherein at least a section of a particular path of the at least one of the sample and the reference is non-reciprocal.

10. The system according to claim 1, wherein the reference receives radiation via a path that is different from a path along which the radiation is transmitted from the reference.

11. The system according to claim 9, wherein the reference is a transmissive reference.

12. The system according to claim 1, wherein, after modifying the length, the computer processing arrangement performs at least one of procedures (I)-(IIIA) based on a new position of the reference.

13. The system according to claim 1, wherein the computer processing arrangement modifies the length of the reference using a controllable parameter.

14. The system according to claim 13, wherein the controllable parameter is a responsiveness parameter which is used to dynamically control a level of modification of the length of the reference.

15. The system according to claim 1, wherein the at least one portion includes a feature of the sample, and wherein the computer processing arrangement determines the lateral position of the feature.

16. The system according to claim 1, wherein the lateral information includes flow information within the at least one portion of the sample.

17. The system according to claim 1, wherein the lateral information includes at least one of birefringence information and polarization information associated with the at least one portion of the sample.

18. The system according to claim 1, wherein the lateral information includes spectroscopic information of the at least one portion of the sample.

19. The system according to claim 1, wherein the lateral information includes intensity information of the at least one portion of the sample.

20. The system according to claim 1, wherein the computer processing arrangement modifies a lateral scan range of the sample based on the lateral position.

21. The system according to claim 20, wherein, after modifying the lateral scan range, the computer processing arrangement performs at least one of procedures (I)-(III) based on a new lateral scan range.

22. The system according to claim 14, wherein the computer processing arrangement modifies the lateral scan range using a controllable parameter.

23. The system according to claim 22, wherein the controllable parameter is a responsiveness parameter which is used to dynamically control a level of modification of the lateral scan range.

24. The system according to claim 1, wherein the computer processing arrangement generates an image of the at least one portion of the sample based on at least one of the depth information or the lateral information of the at least one portion of the sample, and wherein the modification of the length of the reference is performed during the generation of the image.

25. A process to determine at least one position of at least one portion of a sample, comprising:
   obtaining information associated with the at least one portion of the sample, the at least one portion being associated with an interference signal that includes a first electro-magnetic radiation received from the sample and a second electro-magnetic radiation received from a reference;
   obtaining at least one of depth information or lateral information of the at least one portion of the sample;
   applying at least one weight function to the at least one of the depth information or the lateral information so as to generate resulting information;
   with a computer arrangement, ascertaining a particular information which is at least one of a surface position, a lateral position or a depth position of the at least one portion of the sample based on the resulting information; and
   modifying a length of the reference based on the particular information.

26. The method according to claim 25, further comprising generating an image of the at least one portion of the sample based on at least one of the depth information or the lateral information of the at least one portion of the sample, and wherein the modification of the length of the reference is performed during the generation of the image.

27. A software arrangement stored on a hardware storage arrangement and adapted to determine at least one position of at least one portion of a sample, comprising:
   a first set of instructions which, when executed by a computer processing arrangement, obtains information associated with the at least one portion of the sample, the at least one portion being associated with an interference signal that includes a first electro-magnetic radiation received from the sample and a second electro-magnetic radiation received from a reference;
   a second set of instructions which, when executed by the computer processing arrangement, obtains at least one of depth information or lateral information of the at least one portion of the sample;
   a third set of instructions which, when executed by the computer processing arrangement, applies at least one weight function to the at least one of the depth information or the lateral information so as to generate resulting information;

a fourth set of instructions which, when executed by the computer processing arrangement, ascertains a particular information which is at least one of a surface position, a lateral position or a depth position of the at least one portion of the sample based on the resulting information; and a further set of instructions which, when executed by the computer processing arrangement, causes a modification of a length of the reference based on the particular information.

28. The software arrangement according to claim 27, wherein at least one of the depth information or the lateral information includes flow information within the at least one portion of the sample.

29. The software arrangement according to claim 27, wherein at least one of the depth information or the lateral information includes at least one of birefringence information and polarization information associated with the at least one portion of the sample.

30. The software arrangement according to claim 27, wherein at least one of the depth information or the lateral information includes spectroscopic information of the at least one portion of the sample.

31. The software arrangement according to claim 27, wherein the depth information includes intensity information of the at least one portion of the sample.

32. The software arrangement according to claim 27, further comprising a fifth set of instructions which, when executed by the computer processing arrangement, after the particular information is ascertained, at least one of estimates or predicts at least one of the surface position, the lateral position and the depth position as a function of the particular information.

33. The software arrangement according to claim 32, wherein at least one of second through fourth sets of instructions are executed to obtain a set of data associated with the particular information, and wherein the fourth set is executed based on the set of data.

34. The software arrangement according to claim 27, wherein at least one of the depth information or the lateral information includes intensity information of the at least one portion of the sample.

35. The software arrangement according to claim 27, further comprising a delay arrangement associated with at least one the sample and the reference, and facilitates variable transmissive optical paths therein.

36. The software arrangement according to claim 27, wherein at least a section of a particular path of the at least one of the sample and the reference is non-reciprocal.

37. The software arrangement according to claim 27, wherein the reference receives radiation via a path that is different from a path along which the radiation is transmitted from the reference.

38. The software arrangement according to claim 36, wherein the reference is a transmissive reference.

39. The software arrangement according to claim 27, wherein, after modifying the length, at least one of second through fourth sets are executed based on a new position of the reference.

40. The software arrangement according to claim 27, further comprising an eighth set of instructions which, when executed by the computer processing arrangement, modifies the length of the reference using a controllable parameter.

41. The software arrangement according to claim 40, wherein the controllable parameter is a responsiveness parameter which is used to dynamically control a level of modification of the length of the reference.

42. The software arrangement according to claim 27, wherein the at least one portion includes a feature of the sample, and wherein the computer processing arrangement is configured to determine the lateral position of the feature.

43. The software arrangement according to claim 27, wherein the lateral information includes flow information within the at least one portion of the sample.

44. The system according to claim 27, wherein the lateral information includes at least one of birefringence information and polarization information associated with the at least one portion of the sample.

45. The software arrangement according to claim 27, wherein the lateral information includes spectroscopic information of the at least one portion of the sample.

46. The system according to claim 27, wherein the lateral information includes intensity information of the at least one portion of the sample.

47. The software arrangement according to claim 27, further comprising a eighth set of instructions which, when executed by the computer processing arrangement, modifies a lateral scan range of the sample based on the lateral position.

48. The software arrangement according to claim 47, wherein, after modifying the lateral scan range, the second through fourth sets are executed based on a new lateral scan range.

49. The software arrangement according to claim 27, further comprising a ninth set of instructions which, when executed by the computer processing arrangement, modifies the lateral scan range using controllable parameter.

50. The software arrangement according to claim 49, wherein the controllable parameter is a responsiveness parameter which is used to dynamically control a level of modification of the lateral scan range.

51. The software arrangement according to claim 27, further comprising a ninth set of instructions which, when executed by the computer processing arrangement, generates an image of the at least one portion of the sample based on at least one of the depth information or the lateral information of the at least one portion of the sample, and wherein the modification of the length of the reference is performed during the generation of the image.

* * * * *